US007958653B2

(12) United States Patent
Howlett et al.

(10) Patent No.: US 7,958,653 B2
(45) Date of Patent: Jun. 14, 2011

(54) CUSHIONED ORTHOTIC

(75) Inventors: Harold A. Howlett, Horn Lake, MS (US); Bin Xia, Germantown, TN (US); Philip Yang, Memphis, TN (US)

(73) Assignee: Schering-Plough Healthcare Products, Inc., Memphis, TN (US)

( * ) Notice: Subject to any disclaimer, the term of this patent is extended or adjusted under 35 U.S.C. 154(b) by 930 days.

(21) Appl. No.: 11/524,979

(22) Filed: Sep. 21, 2006

(65) Prior Publication Data
US 2008/0072461 A1    Mar. 27, 2008

(51) Int. Cl.
A43B 13/38    (2006.01)
(52) U.S. Cl. .................. 36/44; 36/35 R; 36/43
(58) Field of Classification Search .......... 036/43, 036/44, 37, 35 R
See application file for complete search history.

(56) References Cited

U.S. PATENT DOCUMENTS

| | | | |
|---|---|---|---|
| 1,281,987 A | 10/1918 | McSweeney | |
| 2,055,072 A | 9/1936 | Everston | |
| 2,221,202 A | 11/1940 | Ratcliff | |
| 2,863,231 A | 12/1958 | Jones | |
| 3,233,348 A * | 2/1966 | Gilkerson | 36/44 |
| 3,859,740 A | 1/1975 | Kemp | |
| 4,124,946 A * | 11/1978 | Tomlin | 36/43 |
| 4,168,585 A | 9/1979 | Gleichner | |
| 4,408,402 A | 10/1983 | Looney | |
| 4,494,321 A | 1/1985 | Lawlor | |
| 4,510,700 A | 4/1985 | Brown | |
| 4,648,923 A | 3/1987 | Chapnick | |
| 4,686,993 A | 8/1987 | Grumbine | |
| 4,688,338 A | 8/1987 | Brown | |
| 4,702,255 A | 10/1987 | Schenkl | |
| D296,493 S | 7/1988 | Diaz | |
| 4,782,605 A | 11/1988 | Chapnick | |
| 4,823,420 A | 4/1989 | Bartneck | |
| RE33,066 E | 9/1989 | Stubblefield | |
| 4,901,390 A | 2/1990 | Daley | |
| 4,962,593 A | 10/1990 | Brown | |
| 5,014,706 A | 5/1991 | Philipp | |
| 5,015,427 A | 5/1991 | Sosnow | |
| 5,077,915 A | 1/1992 | Gross | |
| 5,092,060 A | 3/1992 | Frachey et al. | |
| 5,170,572 A | 12/1992 | Kantro | |

(Continued)

FOREIGN PATENT DOCUMENTS

DE    201 19 402 U1    3/2002

(Continued)

OTHER PUBLICATIONS

International Search Report for PCT/US2007/020475 (Apr. 29, 2008)—6 Pages.

(Continued)

Primary Examiner — Marie Patterson
(74) Attorney, Agent, or Firm — Matthew J. Golden

(57) ABSTRACT

An orthotic is disclosed. The orthotic may include a cushioning layer configured to extend from at least the metatarsal region to the proximal heel region, the cushioning layer having a heel region with a protruding heel piece integrally molded as part of the cushioning layer. The orthotic may also include an outer shell layer fixedly coupled to the cushioning layer, the outer shell layer extending longitudinally from at least the medial cuneiform-first metatarsal joint region to the calcaneus bone region of the user, the outer shell layer configured to receive the protruding heel piece.

11 Claims, 18 Drawing Sheets

U.S. PATENT DOCUMENTS

| | | |
|---|---|---|
| 5,175,946 A | 1/1993 | Tsai |
| 5,212,894 A | 5/1993 | Paparo |
| 5,282,326 A | 2/1994 | Schroer et al. |
| 5,311,677 A * | 5/1994 | Mann et al. ............ 36/107 |
| 5,369,896 A | 12/1994 | Frachey et al. |
| D357,349 S | 4/1995 | Vasyli |
| D358,249 S | 5/1995 | Vasyli |
| 5,435,077 A | 7/1995 | Pyle |
| 5,438,768 A | 8/1995 | Bauerfeind |
| D367,164 S | 2/1996 | Fisher et al. |
| 5,542,196 A | 8/1996 | Kantro |
| 5,611,153 A | 3/1997 | Fisher et al. |
| 5,746,011 A | 5/1998 | Hedstrom |
| 5,918,383 A | 7/1999 | Chee |
| 5,933,984 A | 8/1999 | Carlson et al. |
| 5,951,935 A | 9/1999 | Healy et al. |
| 6,000,147 A | 12/1999 | Kellerman |
| 6,041,521 A | 3/2000 | Wong |
| 6,041,524 A | 3/2000 | Brooks |
| 6,098,319 A * | 8/2000 | Epstein |
| 6,125,557 A * | 10/2000 | Brown |
| 6,131,311 A * | 10/2000 | Brown et al. ............ 36/43 |
| 6,145,220 A * | 11/2000 | Johnson et al. ............ 36/34 R |
| 6,233,847 B1 * | 5/2001 | Brown ............ 36/44 |
| 6,247,250 B1 * | 6/2001 | Hauser |
| 6,269,555 B1 * | 8/2001 | Brown |
| 6,282,816 B1 * | 9/2001 | Rosendahl |
| 6,301,805 B1 * | 10/2001 | Howlett et al. ............ 36/43 |
| 6,301,807 B1 * | 10/2001 | Gardiner |
| 6,315,786 B1 * | 11/2001 | Smuckler |
| 6,345,455 B1 * | 2/2002 | Greer, Jr. et al. |
| 6,408,543 B1 * | 6/2002 | Erickson et al. ............ 36/100 |
| 6,508,017 B1 * | 1/2003 | DeBarro et al. |
| 6,519,874 B1 * | 2/2003 | Dean ............ 36/30 R |
| 6,557,273 B2 * | 5/2003 | Polifroni |
| D475,184 S | 6/2003 | Polifroni |
| 6,594,922 B1 * | 7/2003 | Mansfield et al. |
| 6,601,320 B1 * | 8/2003 | Brown |
| 6,604,301 B1 * | 8/2003 | Manoli, II et al. |
| 6,618,960 B2 * | 9/2003 | Brown ............ 36/44 |
| 6,691,432 B2 * | 2/2004 | Masseron |
| 6,802,138 B2 * | 10/2004 | McManus |
| 6,854,199 B2 * | 2/2005 | Polifroni |
| 6,931,763 B2 * | 8/2005 | Bray, Jr. et al. |
| 7,421,808 B2 * | 9/2008 | Baier et al. ............ 36/107 |
| 7,484,319 B2 * | 2/2009 | Cheskin et al. ............ 36/44 |
| 2002/0050080 A1 * | 5/2002 | Vasyli |
| 2002/0083618 A1 * | 7/2002 | Erickson et al. ............ 36/44 |
| 2003/0009915 A1 | 1/2003 | Bacon |
| 2003/0061733 A1 | 4/2003 | Karsten |
| 2003/0140523 A1 | 7/2003 | Issler |
| 2004/0020078 A1 | 2/2004 | Bray, Jr. |
| 2004/0025376 A1 | 2/2004 | Grisoni et al. |
| 2004/0181976 A1 | 9/2004 | Copeskey et al. |
| 2004/0194344 A1 | 10/2004 | Tadin |
| 2005/0044751 A1 | 3/2005 | Alaimo et al. |
| 2005/0066545 A1 | 3/2005 | Peoples |
| 2005/0108899 A1 | 5/2005 | Kielt et al. |
| 2005/0223604 A1 | 10/2005 | Neuner |
| 2007/0107261 A1 * | 5/2007 | Cheskin et al. ............ 36/44 |
| 2007/0289170 A1 * | 12/2007 | Avent et al. ............ 36/166 |

FOREIGN PATENT DOCUMENTS

| | | |
|---|---|---|
| EP | 0 173 396 A2 | 8/1985 |
| WO | WO 2003/037124 A1 | 5/2003 |

OTHER PUBLICATIONS

Written Opinion for PCT/US2007/020475 (Filing Date Sep. 21, 2007)—10 Pages.

* cited by examiner

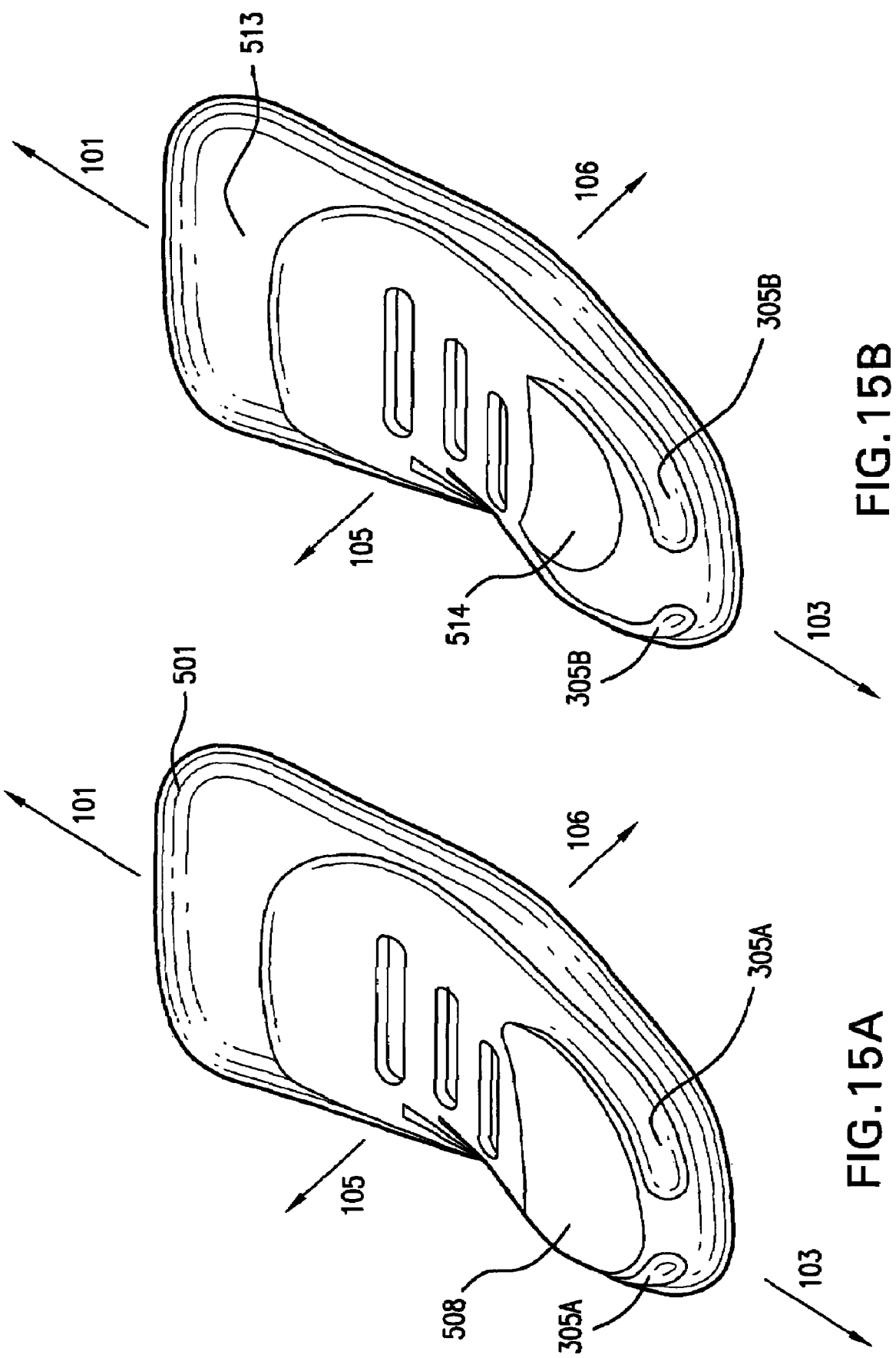

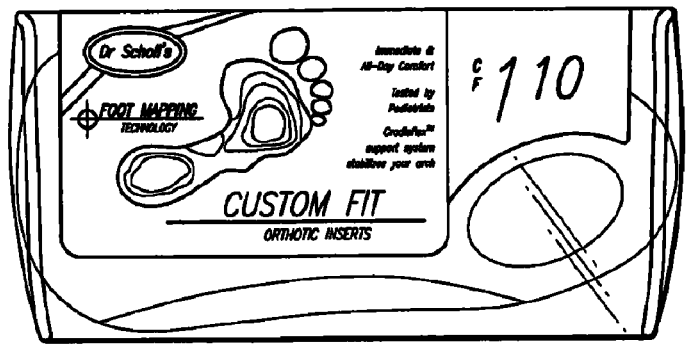
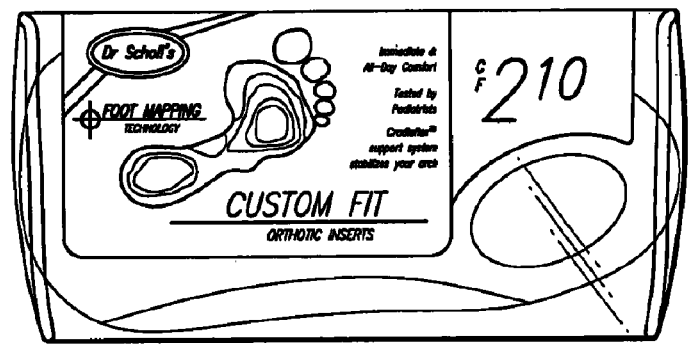
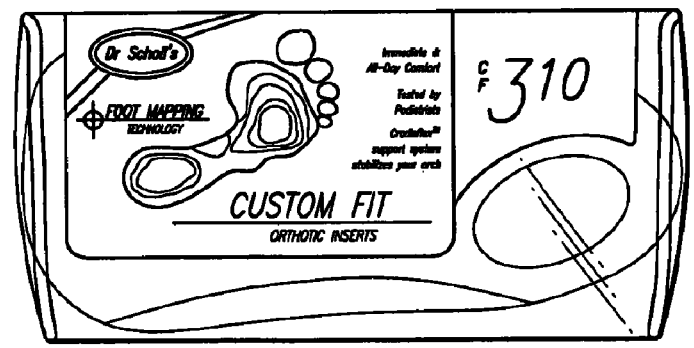
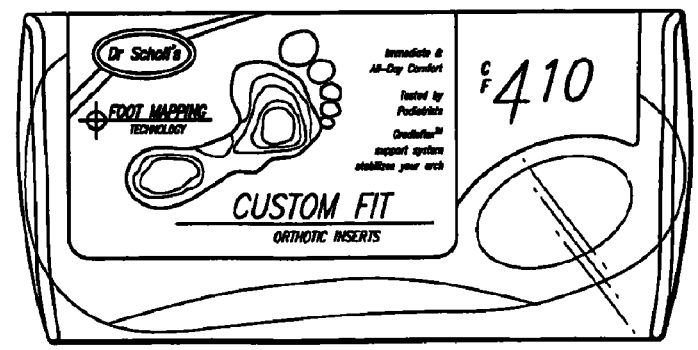
FIG. 16B

CUSHIONED ORTHOTIC

BACKGROUND

Conventional footwear inserts, such as orthotics, are typically provided to users to meet a particular user's needs. Some of these needs may include cushioning, arch support, and pronation control.

Many known orthotics are intended to be custom-made for a user. Custom-made orthotics tend to be relatively expensive, and may require a trip to a special supplier, e.g., a podiatrist, for measurement and fitting. Custom orthotics may also have relatively short useful lives. In some situations, making custom orthotics more durable or providing greater support may also make them heavier, bulkier, or less comfortable.

Pre-manufactured orthotics and shoe inserts are also known. These are typically significantly less expensive than custom orthotics. Pre-manufactured orthotics and inserts include U.S. Pat. Nos. 6,286,232, 6,301,805, 6,481,120, and 6,598,321. Some of pre-manufactured orthotics that provide good support may have poor cushioning properties. Other inserts that have good cushioning properties may offer less support. Some of the known orthotics may have good cushioning and support characteristics but may be relatively expensive to manufacture. In addition, such pre-manufactured orthotics are typically offered only in a limited number of variations, e.g., a single size for men and a single size for women, to minimize stocking and manufacturing costs. However, the population of potential purchasers may have a broad range of preferences for comfort and support.

BRIEF DESCRIPTION OF DRAWINGS

FIGS. 15A and 15B depicts the bottom perspectives of a fifth and sixth example orthotics, according to a fourth alternative example embodiment of the present invention.

FIG. 16B illustrates an example display set of pre-manufactured orthotics, according to an example embodiment of the present invention.

DETAILED DESCRIPTION OF EXAMPLE EMBODIMENTS

Figure 1:
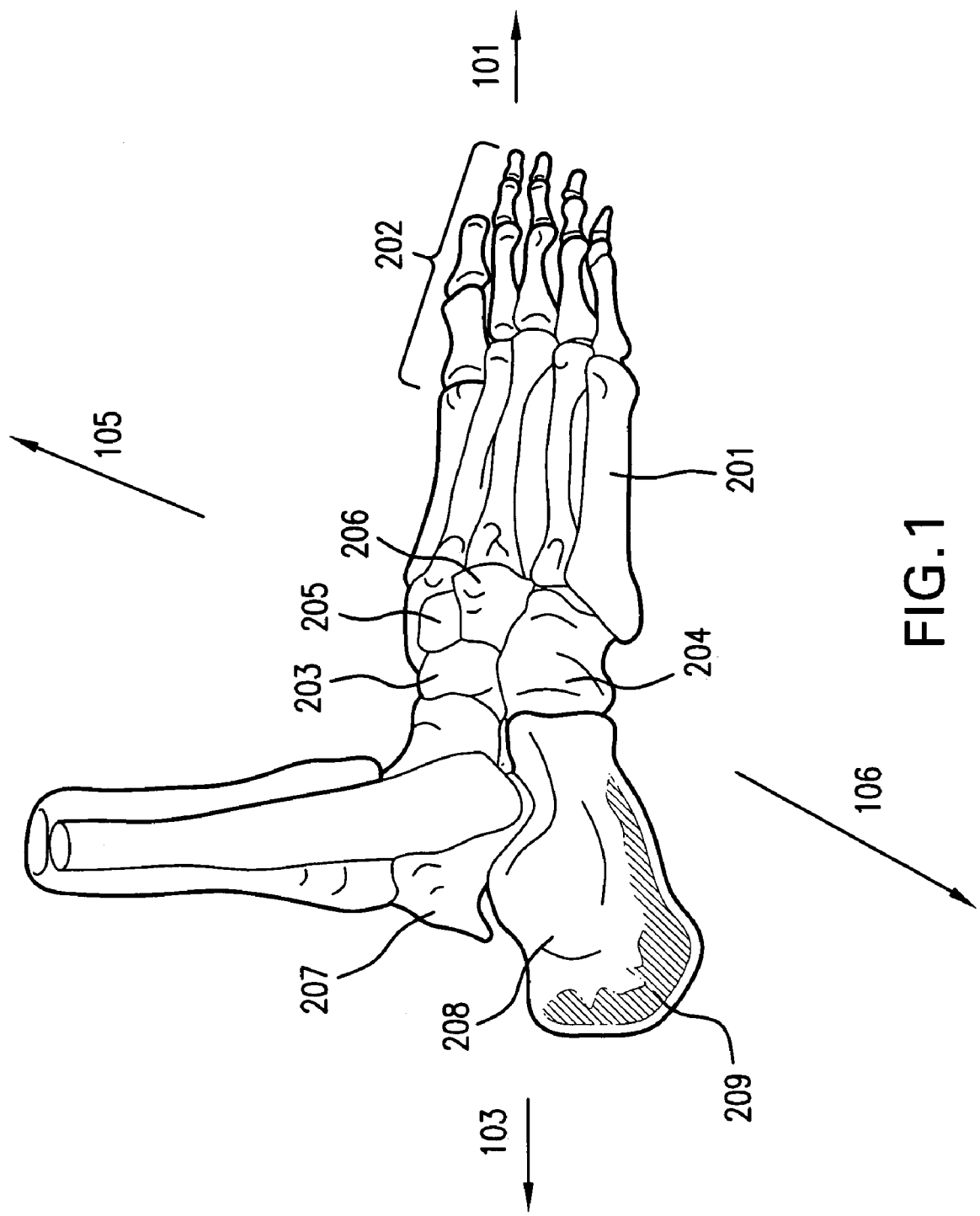
FIG. 1 depicts the framework of a typical human foot.

Some example orthotics, according to some example embodiments of the present invention, include cushion orthotics that provide a balance of support and comfort, while minimizing manufacturing cost. A cushioning layer may be provided for comfort and cushioning, while a shell layer provides support and stability. In particular, by only partly underlying a cushioning layer with a more rigid support shell, maximum cushioning can be provided in areas where the support structure is not present, while still providing support and stability in other areas. For example, it may be desirable to provide cushioning in the heel region and parts of the forefoot, while providing arch support in the center of the foot. The use of a relatively harder arch support insert between the cushioning layer and the outer shell layer provides additional arch support which may be easily varied in different versions of the example orthotic by changing the dimension or properties of the arch support insert, while minimizing the number of different types of components required.

Some example orthotics, according to some example embodiments of the present invention, have been found particularly well-suited to being provided with different sizes and different arch supports. By combining several variations in size and arch support, an acceptable degree of fit, comfort, and support can be provided for the vast majority of potential users with only a limited number of models, e.g., 14 different models. These 14 different models may be provided using only four variants of outer shell layer, seven variants of the cushioning layer, and eight variants of an arch support, greatly reducing manufacturing and inventory costs.

In some example orthotics, according to some example embodiments of the present invention, different materials may be combined for different types of support and cushioning needed for different foot conditions and in different foot regions, e.g., the example orthotic may have support for the medial arch, and cushioning for the heel regions, with or without cushioning at the forefoot region. In some example orthotics according to some example embodiments of the present invention, the "cushion" at the heel region may include an area that covers the entire heel, or part of the heel region, without being enclosed by the outer shell layer. In addition, the example orthotic may be constructed so as to provide optimal support for users performing different activities.

One example embodiment of the present invention is an orthotic. The orthotic may include a covering layer on the top surface, a foam cushioning layer fixedly coupled to the covering layer, the foam cushioning layer configured to extend from at least the proximal metatarsal region to the proximal heel region, the cushioning layer is at its thinnest at the proximal region, thickest at the proximal heel region, the cushioning layer having a protruding heel piece integrally molded as part of the cushioning layer at the proximal heel region, and an upturned medial flange extending towards the proximal heel portion, wrapping around to the opposite lateral side, and tapering towards the distal forefoot portion. The orthotic may also include an outer shell layer fixedly coupled to the cushioning layer, the outer shell layer configured to extend longitudinally from at least the medial cuneiform-first metatarsal joint region to the calcaneus bone region of the user, the outer shell layer further having an upturned flange on the medial side, parallel to the upturned medial flange of the cushioning layer, an enclosure defining an aperture therethrough at the heel region, the enclosure configured to receive the integral protruding heel piece of the cushioning layer, and an inner shell insert layer operably attached between the cushioning layer and the outer shell layer, the inner shell insert layer extending from at least the medial cuneiform-first metatarsal joint region to the talus-navicular joint region of the user.

Another example embodiment of the present invention may be an article of manufacture. The article of manufacture may include a display and a set of pre-manufactured orthotic removably disposed on the display, the set of pre-manufactured orthotics including a plurality of different orthotic models, the plurality of orthotic models including models with different respective lengths and models with different respective levels of arch support, wherein the plurality of orthotic models includes 14 different models, the models including a first model with a shortest length, a softest cushioning layer, and a lowest level of arch support; a second model with the shortest length, the softest cushioning layer, and a higher level of arch support; a third model with the shortest length, a firmer cushioning layer, and the lowest level of arch support; a fourth model with the shortest length, the firmer cushioning layer, and the higher level of arch support; a fifth model with a second length longer than the shortest length, the softest cushioning layer, and the lowest level of arch support; a sixth model with the second length, the softest cushioning layer, and the higher level of arch support; a seventh model with the second length, the firmer cushioning layer, and the lowest level of arch support; an eighth model with the second length, the firmer cushioning layer, and the higher level of arch support; a ninth model with a third length longer than the second length, the softest cushioning layer, and the lowest level of arch support; a tenth model with the third length, the softest cushioning layer, and the higher level of arch support; an eleventh model with the third length, the firmer cushioning layer, and the lowest level of arch support; a twelfth model with the third length, the firmer cushioning layer, and the higher level of arch support; a thirteenth model with the longest length, the firmer cushioning layer, and the lowest level of arch support; a fourteenth model with the longest length, the firmer cushioning layer, and the higher level of arch support. In addition, for each of the example orthotic models, the arch supports may be of different levels for either the inner shell or outer shell layers.

Another example embodiment of the present invention may be an orthotic. The orthotic may include a cushioning layer having a heel region with a protruding heel piece integrally molded as part of the cushioning layer; and an outer shell layer fixedly couple to the cushioning layer, the outer shell layer having an enclosure defining an aperture therethrough at the heel region, the enclosure configured to receive the protruding heel piece. The orthotic may also optionally include an inner shell layer operably attached between the outer shell layer, and the cushioning layer, the inner shell layer configured to underlie and support the arch region of the user.

Another example embodiment of the present invention may be an orthotic. The orthotic may include a cushioning layer configured to extend from at least the metatarsal region to the proximal heel region, the cushioning layer having a heel region with a protruding heel piece integrally molded as part of the cushioning layer; and an outer shell layer fixedly coupled to the cushioning layer, the outer shell layer extending longitudinally from at least the medial cuneiform-first metatarsal joint region to the calcaneus bone region of the user, the outer shell layer configured to receive the protruding heel piece. The orthotic may optionally be ¾ in length and extend forward from the outer shell layer. The orthotic may optionally be full length and extends forward from the outer shell layer. The orthotic may also optionally include an inner shell layer operably attached between the outer shell layer, and the cushioning layer, the inner shell layer configured to underlie and support the arch region of the user. The inner shell layer may be configured to extend from at least the medial cuneiform-first metatarsal joint region to the distal end of the protruding heel piece. The inner shell layer may be made from a thermoplastic material, e.g., thermoplastic polyurethane; foamed materials, e.g. EVA, polyurethane foam; or thermoset materials, e.g., composites. The cushioning layer may be formed as a hell cup at the proximal end. The outer shell layer may optionally further include an upturned flanged on the medial side. The outer shell layer may further optionally include a plurality of perforations in the mid portion of the outer shell layer. The perforations in the mid portion of the outer shell layer may optionally include a plurality of parallel slots extending from the medial side to the lateral side.

Another example embodiment of the present invention may be an orthotic. The orthotic may include a covering layer on a top surface; a foam cushioning layer fixedly coupled to the covering layer, the foam cushioning layer is configured to extend from at least the proximal metatarsal region to the proximal heel region, the cushioning layer is thinnest at the distal forefoot region and thickest at the heel region, the cushioning layer having an upwardly raised convex protrusion between the second and fourth metatarsal, the cushioning layer further having a heel region with a protruding heel piece integrally formed as part of the foam cushioning layer, the protruding heel piece supporting the entire heel region and an upturned medial flange extending towards the proximal heel portion, wrapping around to the opposite lateral side, and tapering towards the distal forefoot portion. The orthotic may also include an outer shell layer fixedly coupled to the foam cushioning layer, the outer shell layer is configured to extend longitudinally from at least the medial cuneiform-first metatarsal joint region to the talus-navicular bone region, extending on either side around the calcaneus bone portion, the outer shell layer at the calcaneuous bone region cut out to form an enclosure defining an aperture therethrough for receiving the protruding heel piece, the outer shell layer extending on either side of the calcaneous region a pair of projecting extensions having a first end and a second end, the projecting extensions embracing the heel piece on either side with the first end and the second end terminating just behind the heel region, the outer shell layer further having an upturned medial flange, parallel to the upturned flange of the cushioning layer; and an inner shell insert layer operably attached between the cushioning layer and the outer shell layer, the inner shell insert layer extending from at least the medial cuneiform-first metatarsal joint region to the talus-navicular joint region of the user.

Another example embodiment of the present invention may be an orthotic. The orthotic may include a cushioning layer having a heel region with a protruding heel piece integrally formed as part of the cushioning layer; an outer shell layer fixedly coupled to the cushioning layer, the outer shell layer having a pair of projecting extensions, having a first end and second end, and embracing an enclosure defining an aperture therethrough at the heel region. The orthotic may also optionally include an inner shell layer operably attached between the outer shell layer, and the cushioning layer, the inner shell layer configured to underlie and support the arch region of the user.

Another example embodiment of the present invention may be an orthotic. The orthotic may include a cushioning layer having a heel region with a protruding heel piece integrally formed as part of the cushioning layer; and an outer shell layer fixedly attached to the cushioning layer, the outer shell layer extending longitudinally from at least the medial cuneiform-first metatarsal joint region to the talus-navicular region, the outer shell layer having a pair of projecting extensions on either side of the calcaneus bone region, and an enclosure defining an aperture therethrough at the heel region for receiving the protruding heel piece of the cushioning layer. The outer shell layer may have an upturned medial flange. The outer shell layer may extend to form a pair of projecting extensions on either side of the calcaneus bone region may not be joined at the back of the heel region. Alternatively, the pair of projecting extensions on either side of the calcaneus bone region may be joined at the back of the heel region. The orthotic may also optionally include an inner shell insert layer operably attached between the cushioning layer, and the outer shell layer. The foam cushioning layer of the orthotic may include a raised convex protrusion at the distal forefoot region between the second to fourth metatarsal.

Another example embodiment of the present invention may be an orthotic. The orthotic may include a covering layer on a top surface; a foam cushioning layer fixedly coupled to the covering layer, the foam cushioning layer is configured to extend from at least the proximal metatarsal region to the proximal heel region, the cushioning layer is thinnest towards the distal forefoot region and thickest at the heel region, the cushioning layer having an upwardly raised convex protrusion between the second and fourth metatarsal, the cushioning layer further having a heel region with a protruding heel piece integrally formed as part of the foam cushioning layer, the protruding heel piece supporting the entire heel region and an upturned medial flange extending towards the proximal heel portion, wrapping around to the opposite lateral side, and tapering towards the distal forefoot portion. The orthotic may also include an outer shell layer fixedly coupled to the foam cushioning layer, the outer shell layer is configured to extend longitudinally from at least the medial cuneiform-first metatarsal joint region to the talus-navicular bone region, extending on either side around the calcaneus bone portion, the outer shell layer at the calcaneuous bone region cut out to form an enclosure defining an aperture therethrough for receiving the protruding heel piece, the outer shell layer extending on either side of the calcaneuos region a pair of projecting extensions having a first end and a second end, the projecting extensions embracing the heel piece on either side with the first end and the second end joined at the heel region, the outer shell layer further having an upturned medial flange, parallel to the upturned flange of the cushioning layer; and an inner shell insert layer operably attached between the cushioning layer and the outer shell layer, the inner shell insert layer extending from at least the medial cuneiform-first metatarsal joint region to the talus-navicular joint region of the user.

Another example embodiment of the present invention may be a set of pre-manufactured cushioned orthotics. The set of pre-manufactured cushioned orthotics may include a plurality of orthotics, the orthotics each having a cushioning layer and an arch support, the plurality of orthotics including orthotic models having at least two different respective lengths, orthotic models having at least two different respective levels of cushioning layer firmness, and orthotic models having at least two different respective levels of arch support. The set of pre-manufactured cushioned orthotics may include at least two orthotic models of the same length that have arch supports of different respective levels. The set of pre-manufactured cushioned orthotics having different levels of arch support may be made of a flexible polymer with different hardness. The set of pre-manufactured cushioned orthotics may include at least two orthotic models of the same length having arch supports made of different materials. The set of pre-manufactured cushioned orthotics may include arch supports of different materials for an orthotic model of a particular length that may be substantially dimensionally identical. The set of pre-manufactured cushioned orthotics of the longest length may not have the softest cushioning layer. The set of pre-manufactured cushioned orthotics may optionally include ¾-length orthotics. The set of pre-manufactured cushioned orthotics may include orthotic models having fourteen different models with at least four different lengths, at least two levels of cushioning layer firmness, and at least two levels of arch support. For at least one of the lengths, there may be at least four models which may include a first model series with a softest cushioning layer and lowest level of arch support, a second model series with a softest cushioning layer and a higher level of arch support, a third model series with a firmer cushioning layer and a lowest level of arch support, and a fourth model series with a firmer cushioning layer and a higher level of arch support. The set of pre-manufactured cushioned orthotics may include the orthotic model series having 14 different models, the models may have a first model with a shortest length, a softest cushioning layer, and a lowest level of arch support; a second model with the shortest length, the softest cushioning layer, and a higher level of arch support; a third model with the shortest length, a firmer cushioning layer, and the lowest level of arch support; a fourth model with the shortest length, the firmer cushioning layer, and the higher level of arch support; a fifth model with a second length longer than the shortest length, the softest cushioning layer, and the lowest level of arch support; a sixth model with the second length, the softest cushioning layer, and the higher level of arch support; a seventh model with the second length, the firmer cushioning layer, and the lowest level of arch support; an eighth model with the second length, the firmer cushioning layer, and the higher level of arch support; a ninth model with a third length longer than the second length, the softest cushioning layer, and the lowest level of arch support; a tenth model with the third length, the softest cushioning layer, and the higher level of arch support; an eleventh model with the third length, the firmer cushioning layer, and the lowest level of arch support; a twelfth model with the third length, the firmer cushioning layer, and the higher level of arch support; a thirteenth model with the longest length, the firmer cushioning layer, and the lowest level of arch support;

a fourteenth model with the longest length, the firmer cushioning layer, and the higher level of arch support.

Another example embodiment of the present invention may be an article of manufacture. The article of manufacture may include a display; and a set of pre-manufactured orthotic removably disposed on the display, the set of pre-manufactured orthotics including a plurality of different orthotic models, the plurality of orthotic models including models with different respective lengths and models with different respective levels of arch support. The article of manufacture may optionally include orthotics models having a cushioning layer made of different respective levels of cushion firmness. The article of manufacture may include orthotic models having different levels of arch support for different models of orthotic with the same length by having different arch support dimensions. The different levels of arch support for different models of orthotics with the same length may use different arch support materials. The arch supports for different models with the same length may have substantially the same arch support dimension. The different levels of arch support provided for different models of orthotics with the same length may use different arch support materials. The arch supports for different models with the same length may have substantially the same arch support dimension.

The article of manufacture may optionally include orthotics of different lengths and levels of arch support having substantially similar external designs. The article of manufacture may include orthotics that may be ¾-length orthotics. The article of manufacture may include orthotics models with the same size having substantially the same color scheme. The article of manufacture may also include orthotics models with the same support level having substantially the same color scheme. The article of manufacture may optionally include all components of the orthotic models having the same length substantially dimensionally identical.

FIG. 1 depicts the bone framework of a typical human right foot. The view depicts the various directional orientations. The distal axis 101 points away from the point of attachment of the foot to the rest of body, the toes being located in the distal direction from the heel. The proximal axis 103 is the opposite of the distal axis 101, i.e., the heels are in the proximal direction from the toes. The medial axis 105 points to the inner side of the body, towards the opposite foot. The lateral axis 106 is opposite the medial axis 105, and points to the peripheral side of the body. The medial side is the inner side of the foot, while the lateral side is the outside region of the foot, opposite to the medial side. The distal end of the foot, the forefoot, includes the five metatarsal bones 201, along with the phalanges 202 that are the bones of the toes or digits. The midfoot, or the arch region, is formed by five of the seven tarsal bones (not shown), the navicular 203, cuboid 204, the medial cuneiform bone (not shown), the intermediate cuneiform bone 205, and lateral cuneiform bone 206. The midfoot is joined to the forefoot by the tarsometatarsal joints (not shown). The talus 207 and calcaneus 208 bones at the proximal end of the foot make up the hind foot. The calcaneus bone 208 articulates with the cuboid bone 204 to form the calcaneocuboid joint, while the talus bone 207 articulates with the navicular bone 203 forming the talonavicular joint. The proximal part of the calcaneus 208 has a large round projection, the calcaneal tuberosity 209, which forms the back of the heel.

Figure 2:
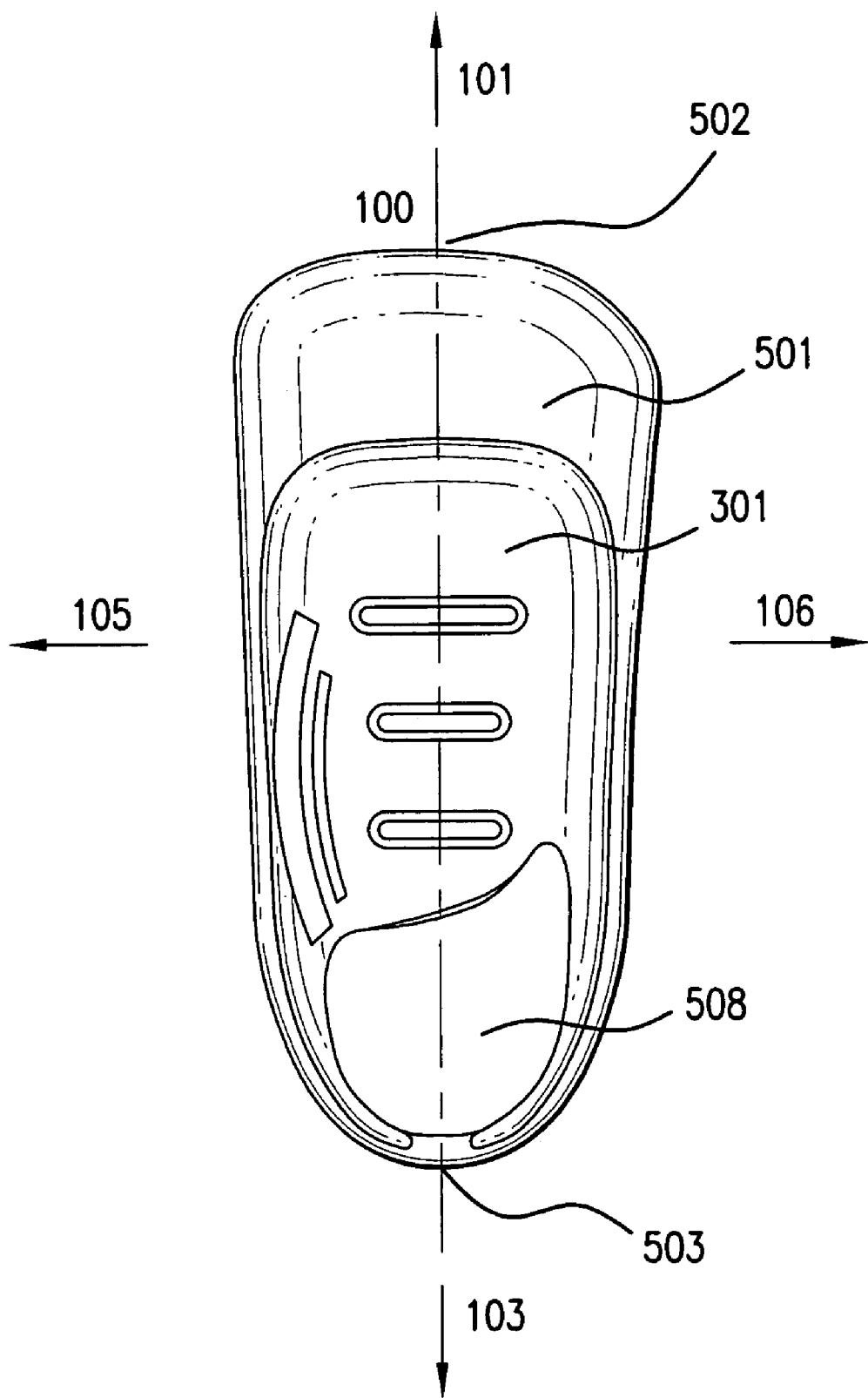
FIG. 2 depicts a bottom view of an example orthotic, according to an example embodiment of the present invention.

FIG. 2 depicts a bottom view of an example orthotic, according to an example embodiment of the present invention. The example shown is for a left foot orthotic. It will be appreciated that the right foot orthotic may be a mirror image along the centerline axis 100. FIG. 2 shows the orientations of the example orthotic in relation to a user's left foot. The example orthotic may be shaped so as to be inserted as an insole in a typical shoe. The orthotic may extend from the distal end 502 to the proximal end 503. The proximal portion of the orthotic lies generally below the heel of the user, with the proximal end 503 generally being slightly behind the proximal end of the bottom of the user's foot. The example orthotic depicted in FIG. 2 may be configured to be "¾-length". The distal portion of the example orthotic is configured to lie generally beneath the metatarsals of the user, when the orthotic is worn in the user's shoe. However, it will be appreciated that the exact location of the distal end 502 of the orthotic with respect to the user's foot when the orthotic is in use may vary depending on the length of the user's foot. It will also be appreciated that a full-length orthotic extending under or past the user's toes may also be provided. Alternatively, a shorter or a "½ length" orthotic, without a heel region, or with a smaller heel region, may be provided. When inserted, the medial portion of the orthotic is configured to lie generally below the medial side of the user's foot, with the medial edge of the orthotic being outside the medial edge of the bottom of the user's foot. Similarly, the lateral portion of the orthotic lies generally below the lateral side of the user's foot, with the lateral edge of the orthotic slightly outside the lateral edge of the bottom of the user's foot.

The example orthotic illustrated in FIG. 2 may include at least two layers: an outer shell layer 301, and the molded cushioning layer 501. It will be appreciated that because of the perspective view in FIG. 2, only the perimeter, the distal, and part of the proximal portions of the molded cushioning layer are visible. The molded cushioning layer may have a protruding heel piece 508. The protruding heel piece 508 extends from the main body of the cushioning layer, so that, in the region where the heel piece 508 is present, the bottom surface of the heel piece forms the bottom surface of the orthotic. It will be appreciated that the heel piece need not protrude so far as to extend past the bottom line formed by the bottom surface of the main body of the outer shell layer 301, although in some alternative configurations, a more pronounced extension of the heel portion may be desirable.

The molded cushioning layer 501 of the example orthotic may be configured so that the distal end 502 extends underneath at least the metatarsal bone region of a user wearing the orthotic. The heel region of the example orthotic may extend, at its proximal end 503 to at least under the heel region of a user wearing the orthotic. It will be appreciated that the example orthotic may alternatively be provided as a full-length variant. The full-length orthotic may extend from under the phalanges of the user to under the heel of the user's foot. The width of the example orthotic may be broadest at the distal end 502. The width of the example orthotic gradually tapers towards the proximal end 503. It will also be appreciated that other cushioning configurations may be employed, e.g., cushions may be provided at only a portion of the orthotic, such as the heel region.

The outer shell layer 301 in FIG. 2, described more fully below, may be manufactured from rigid plastic material. The outer shell layer 301 may provide a relatively rigid support for the foot, particularly at the arch region. The outer shell layer 301 may be configured to extend longitudinally from at least the medial cuneiform-first metatarsal joint region to the calcaneus bone region of the user, when the orthotic is in use. The outer shell layer 301 has a top surface and a bottom surface. The top surface of the outer shell layer 301 may be operably attached to the bottom surface of the molded cushioning layer 501 by gluing the top surface of the outer shell layer 301 to the bottom surface of the molded cushioning layer 501. It will be appreciated that, as an alternative, the outer shell layer 301 may be operably attached to the molded cushioning layer 501 by use of other adhesives, heat, pressure, welding, etc., with or without an inner shell layer described at below.

Figure 3:
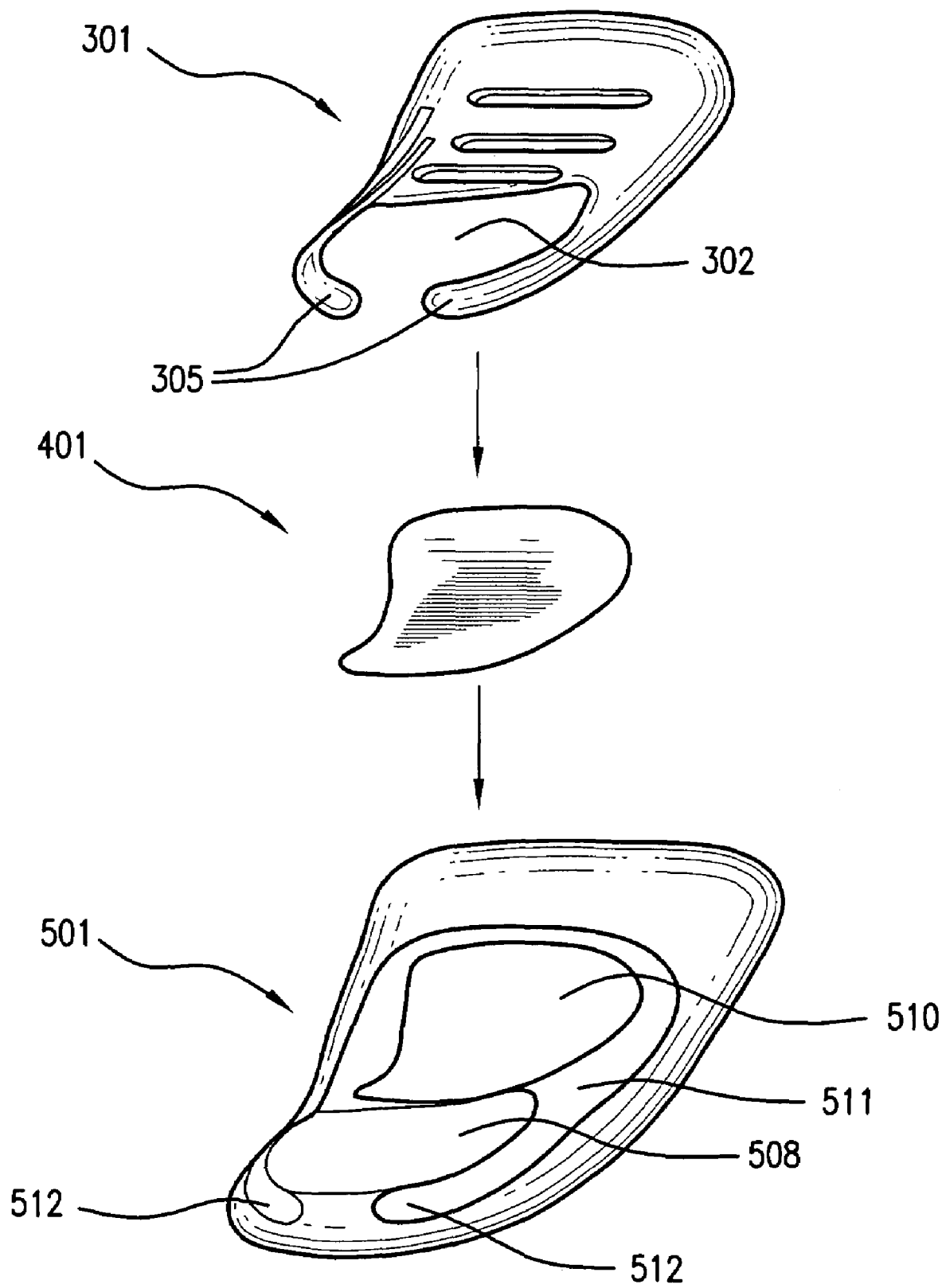
FIG. 3 depicts an exploded view of the example orthotic, according to the example embodiment of the present invention.

FIG. 3 depicts an exploded view of an example orthotic, according to an example embodiment of the present invention. The inner shell layer 401 is operably aligned and attached to the molded cushioning layer 501. The molded cushioning layer 501 has an impression 510 that may be similar in shape to the inner shell layer 401. The inner shell layer 401 may be operably attached to the molded cushioning layer 501 with or without a thermoplastic polyurethane film in between the two layers. The outer shell layer 301 may have a receiving enclosure 302 shown in the top panel of FIG. 3. The outer shell layer 301 may be placed over the inner shell layer 401 and the molded cushioning layer 501. The molded cushioning layer may have an impression 511 that has a similar shape as the outer shell layer 301 and is configured to receive the outer shell layer 301. The edge of the receiving enclosure 302 may define an aperture through the outer shell layer 301. A pair of projecting extensions 305 on either side of the outer shell layer may embrace the outside edges of the heel piece 508. The molded cushioning layer may have an impression 512 similar to that of the projecting extensions. The ends of the projecting extensions 305 at back of the heel piece 508 need not be joined at the back end of the heel region, although they may be.

The different layers of the example orthotic may be operably attached to each other by gluing the layers together as depicted in FIG. 3 by first operably attaching the inner shell insert layer 401 to the molded cushioning layer 501. The outer shell layer 301 may then be attached to the inner shell insert layer/cushioning layer complex. The layers described above may be operably attached to each successive layer by use of an adhesive, heat, pressure, microwave, radiation, and other conventional methods.

Figure 4:
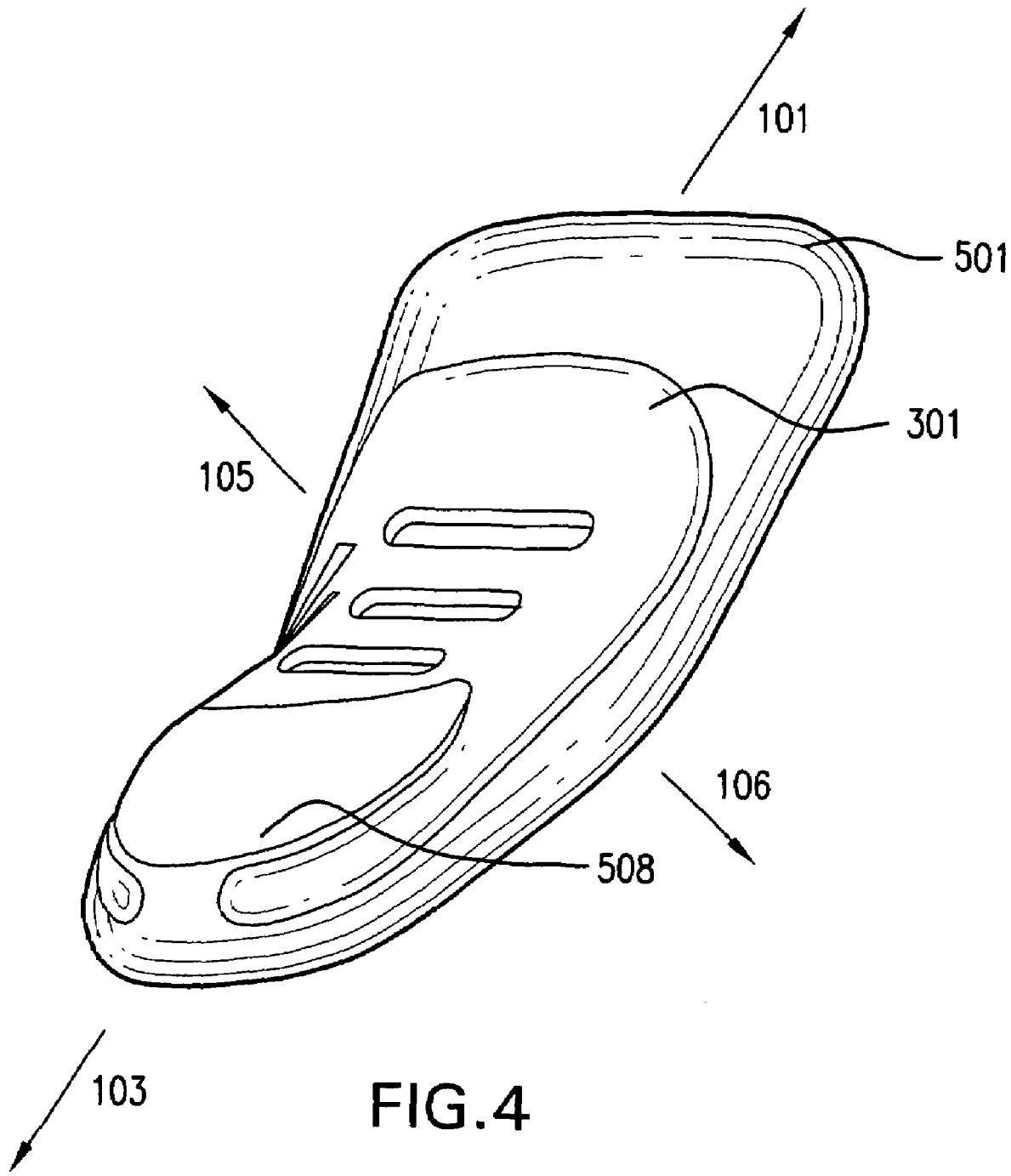
FIG. 4 depicts an isometric bottom perspective of the example orthotic, according to the example embodiment of the present invention.

FIG. 4 depicts an isometric perspective view of the bottom of the example orthotic, according to an example embodiment of the present invention as described in FIGS. 2 and 3 above. The example orthotic shown may have an outer shell layer 301, and a molded cushioning layer 501 having a protruding heel piece 508.

Figure 5:
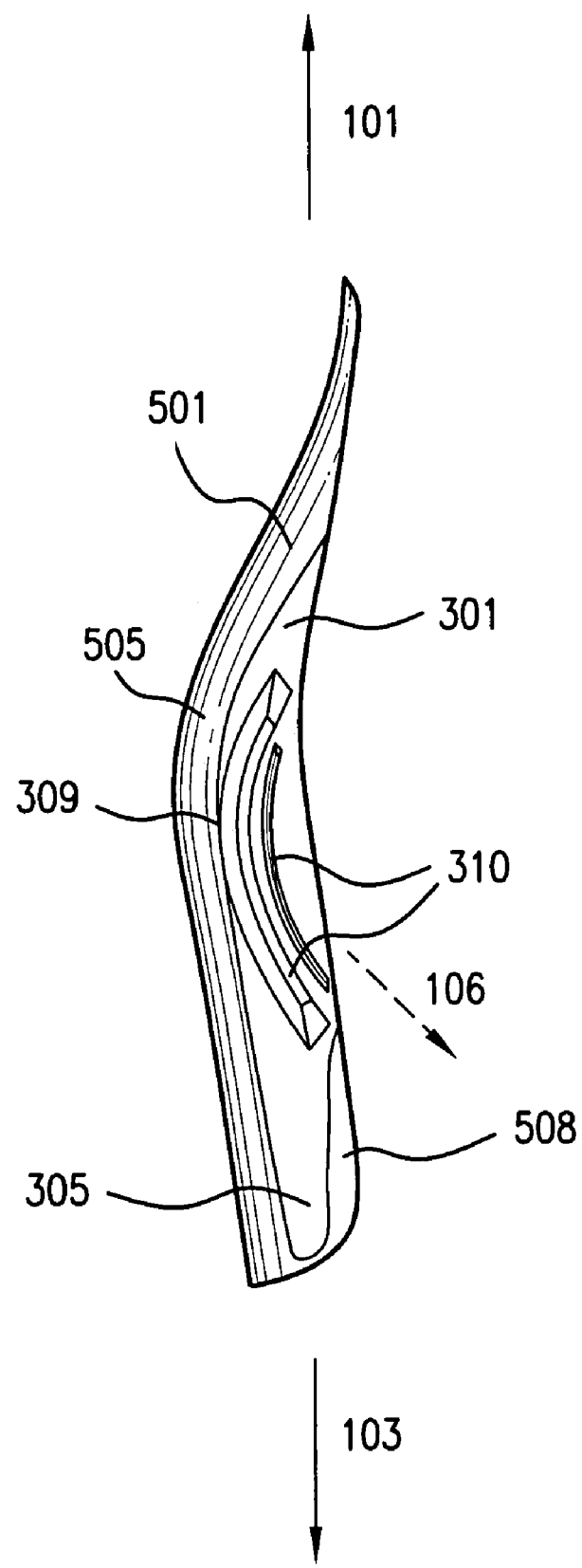
FIG. 5 depicts a medial side view of the example orthotic, according to the example embodiment of the present invention.

FIG. 5 depicts a right side view of the example orthotic according to the example embodiment of the present invention. FIG. 5 shows the molded cushioning layer 501 and the outer shell layer 301 of a left foot orthotic viewed from the right side. The molded cushioning layer 501 at the medial side of the orthotic forms an upturned flange 505 that is parallel to the upturned medial flange of the outer shell layer 309. The outer shell layer 301 may have a pair of curve ribs 310 along the medial side of the upturned medial flange 505. At the proximal end, the protruding heel piece 508 of the molded cushioning layer 501 protrudes through a receiving enclosure defining an aperture through the outer shell layer 301, so as to be approximately flush with the bottom surface of outer shell layer 301 that is adjacent the aperture.

Figure 6:
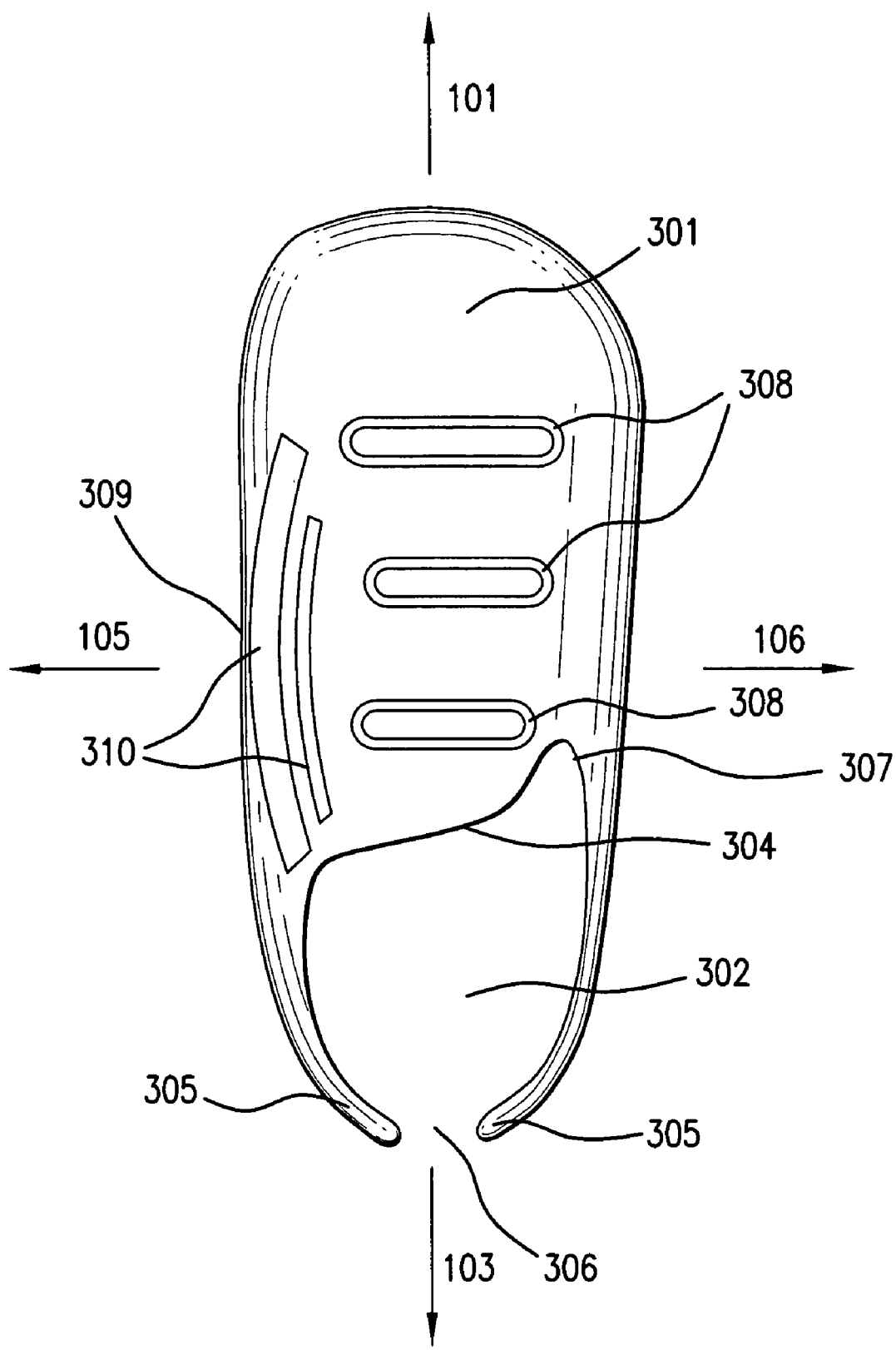
FIG. 6 depicts an outer shell of the example orthotic, according to the example embodiment of the present invention.

FIG. 6 depicts a bottom view of an example outer shell layer, according to the example embodiment of the present invention. The outer shell layer 301 may be configured to extend longitudinally from at least the medial cuneiform-first metatarsal joint region to the calcaneus bone region of a user, when the orthotic is in use.

The example outer shell layer 301 may be constructed from a thermoplastic olefin polymer that may be stiff and flexible, e.g., polyethylene, polypropylene, polyurethane, or elastomers, or a combination of thermoplastic polyurethane and acrylonitrile-butadiene-styrene. One example may be UH-64D20 thermoplastic polyurethane (TPU) from Ure-tech Company, Cheng-Hwa Hsien, Taiwan, Republic of China. Table I, below, includes entries for example outer shell layers for a set of 14 different models of the example orthotic. Each model may have a slightly different thickness and weight. For various models, different polyurethanes may be employed, having different Shore hardness levels which are shown in column 4 of Table I. The higher the Shore hardness number, the greater the resistance to an indenter.

TABLE I

Specification of Example Orthotics for the Outer Shell Layer 301

| Product Nos. | Outer Shell Layer | | |
|---|---|---|---|
| | Weight (g) | Thickness (mm) | Hardness (Duro) |
| 1 | 8.6 ± 1.0 | 1.1 ± 0.2 | 95 ± 5 Shore A |
| 2 | 10.1 ± 1.0 | 1.3 ± 0.2 | 95 ± 5 Shore A |
| 3 | 13.0 ± 1.0 | 1.4 ± 0.2 | 95 ± 5 Shore A |
| 4 | 8.6 ± 1.0 | 1.1 ± 0.2 | 95 ± 5 Shore A |
| 5 | 10.1 ± 1.0 | 1.3 ± 0.2 | 95 ± 5 Shore A |
| 6 | 13.0 ± 1.0 | 1.4 ± 0.2 | 95 ± 5 Shore A |
| 7 | 8.6 ± 1.0 | 1.1 ± 0.2 | 64 ± 5 Shore D |
| 8 | 10.1 ± 1.0 | 1.3 ± 0.2 | 64 ± 5 Shore D |
| 9 | 13.0 ± 1.0 | 1.4 ± 0.2 | 64 ± 3 Shore D |
| 10 | 15.1 ± 1.0 | 1.5 ± 0.2 | 64 ± 5 Shore D |
| 11 | 8.6 ± 1.0 | 1.1 ± 0.2 | 64 ± 5 Shore D |
| 12 | 10.1 ± 1.0 | 1.3 ± 0.2 | 64 ± 5 Shore D |
| 13 | 13.0 ± 1.0 | 1.4 ± 0.2 | 64 ± 5 Shore D |
| 14 | 15.1 ± 1.0 | 1.5 ± 0.2 | 64 ± 5 Shore D |

As shown in Table I, column 4, the outer shell layer 301 may be configured from a thermoplastic polyurethane having a Shore hardness of about 95±5 Shore A to about 64±5 Shore D. The thickness of the outer shell layer 301 may range from about 0.9 mm to about 1.7 mm. (See, column 3). The outer shell layer 301 may weigh from about 7 g to about 16 g (See, column 2). The outer shell layer 301 may be made from polyurethane of different base colors, e.g., red, blue, green, yellow, and combinations of colors. The colors may be chosen to indicate the various models.

The proximal or rear portion of the outer shell layer 301 may be configured to form a receiving enclosure 302 defining an aperture through the outer shell layer 301 for receiving an integrally molded protruding heel piece 508 of the molded cushioning layer 501. The receiving enclosure 302 of the outer shell layer 301 may be configured such that the main body of the outer shell layer 301 terminates at the distal end 304. The receiving enclosure 302 may curve upwards towards the lateral side to form a "spur" 307. It will be appreciated that the receiving enclosure 302 may be an aperture through the outer shell layer 301, the receiving enclosure encompasses the entire portion of the heel region. Alternatively, the receiving enclosure 302 may encompass just the center of the heel region of the cushioning layer, with the projecting portion of the heel region occupying only a portion of the total area of the heel region.

The outer shell layer 301 continues to extend as projecting extensions 305 on both sides of the orthotic towards the back of the heel region to embrace the protruding heel piece 508 of the molded cushioning layer 501. It will be appreciated that the ends of the projecting extensions 305 need not be joined at the back of the heel region, leaving a "gap" 306 between the ends of the projecting extensions 305. The molded cushioning layer 501 may have an exposed area or "gap" 306 at the back of the heel region where the heel region of the cushioning layer is not covered by the projecting extensions 305. However, it will be appreciated that, alternatively, the projecting extensions 305 may be joined at the back of the heel region to form a fully enclosed region for receiving the heel piece.

As depicted in FIG. 6, the outer shell layer 301 may have a plurality of perforations, e.g., a series of slots 308, in the mid portion of the outer shell layer 301. The slots 308 may be located just behind the cuneiform-first metatarsal joint region to the talus-navicular joint region of the user. The slots may be generally parallel to each other. The slots may extend from the medial to the lateral sides of the orthotic. It will be appreciated that, as an alternative, the series of parallel slots may extend diagonally from the medial to the lateral side. Alternatively, the perforations may include a plurality of circular perforations, or a series of wave-like perforations with a generally sinusoidal shape. It will be appreciated that the perforations at the mid portion are not limited to a series of parallel slots, circular or wave-like perforations. It will be appreciated that, alternatively, the outer shell layer 301 may be a continuous piece without any perforations at the mid portion.

On the medial side of the orthotic, the outer shell layer 301 may be configured to have a medial flange 309. The medial flange 309 may turn upwards towards the molded cushioning layer 501. The medial flange 309 may provide support for the arch region of the user's foot and may serve to prevent pronation of the foot. The medial flange 309 of the outer shell layer 301 may have a pair of curved ribs 310 along the sides.

Figure 7:
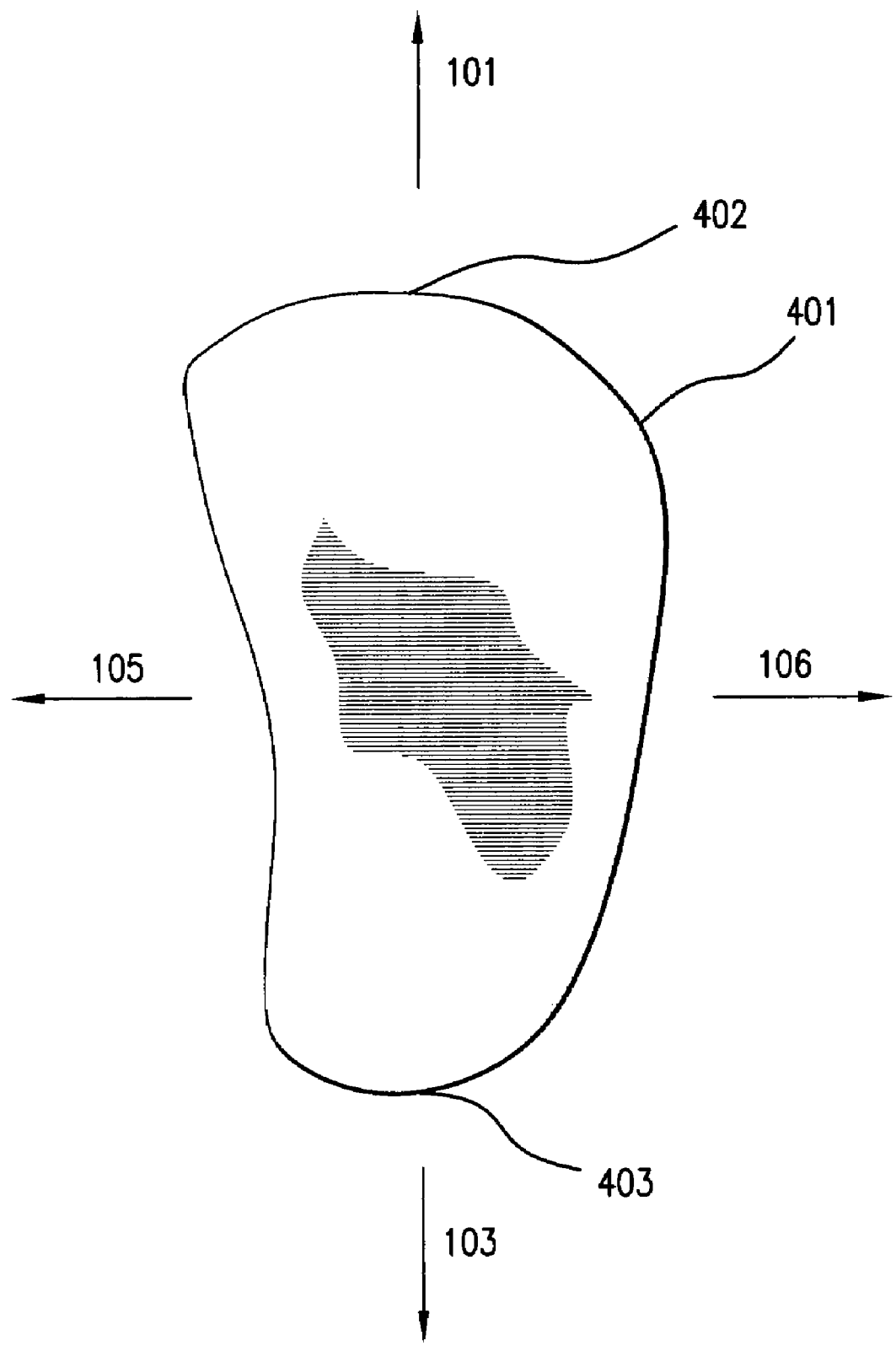
FIG. 7 depicts an inner shell layer of the example orthotic, according to the example embodiment of the present invention.

FIG. 7 depicts an example embodiment of the inner shell layer 401 of the example orthotic for the left foot. The inner shell layer 401 may be shaped like a truncated version of the outer shell layer 301. The inner shell layer 401 may extend longitudinally from at least the medial cuneiform-first metatarsal joint region at the distal end 402 to the proximal end 403. The proximal end 403 of the inner shell layer 401 may abut at least the distal edge 304 of the heel piece where the receiving enclosure 302 of the outer shell layer begins. (See, FIG. 6 above) The inner shell layer 401 may be curved at the medial side. The inner shell layer 401 may be broader at the distal end 402 than at the proximal end 403. The inner shell layer 401 may provide further support for the bottom of the longitudinal arch region (heel to toe) of the foot by providing more rigidity and a spring component to the orthotic.

The inner shell layer 401 may be a molded piece of thermoplastic polyurethane, e.g., Dylon A 9500S from Dahin Co. Ltd., Taipei, Taiwan, Republic of China, having a top surface, and a bottom surface. The inner shell layer 401 may be operably inserted and attached between the outer shell layer 301, and the molded cushioning layer 501. Top surface of the inner shell layer 401 may be operably attached to the bottom surface the molded cushioning layer 501, with or without a thermoplastic polyurethane film. The bottom surface of the inner shell layer 401 may be operably attached to the top surface of the outer shell layer 301, with or without a thermoplastic polyurethane film.

The inner shell layer 401 of the example orthotic in the example embodiment of FIG. 7 may be constructed from a stiff, flexible fiberglass material or olefin polymer, e.g., polyethylene, polypropylene, polyurethane, or elastomer. The inner shell layer may also be constructed using acrylonitrile-butadiene-styrene or a combination of thermoplastic polyurethane and acrylonitrile-butadiene-styrene. The inner shell layer 401 may be constructed from thermoplastic polyurethane having a range of different Shore hardness. Examples of the inner shell layer 401 are shown in Table II. The entries in Table II correspond to the same 14 example orthotic models previously described in Table I.

TABLE II

Specification of Example Orthotics for the Inner Shell Layer 401

| Product Nos. | Inner Shell Layer 401 | | |
|---|---|---|---|
| | Weight (g) | Thickness (mm) | Hardness (Duro) |
| 1 | 3.4 ± 0.5 | 1.0 ± 0.2 | 95 ± 5 Shore A |
| 2 | 4.5 ± 0.5 | 1.1 ± 0.2 | 95 ± 5 Shore A |
| 3 | 5.0 ± 0.5 | 1.1 ± 0.2 | 95 ± 5 Shore A |
| 4 | 3.4 ± 0.5 | 1.0 ± 0.2 | 64 ± 5 Shore D |
| 5 | 4.5 ± 0.5 | 1.1 ± 0.2 | 64 ± 5 Shore D |
| 6 | 5.0 ± 0.5 | 1.1 ± 0.2 | 64 ± 5 Shore D |
| 7 | 3.4 ± 0.5 | 1.0 ± 0.2 | 95 ± 5 Shore A |
| 8 | 4.5 ± 0.5 | 1.1 ± 0.2 | 95 ± 5 Shore A |
| 9 | 5.0 ± 0.5 | 1.1 ± 0.2 | 95 ± 5 Shore A |
| 10 | 5.8 ± 0.5 | 1.1 ± 0.2 | 95 ± 5 Shore A |
| 11 | 3.4 ± 0.5 | 1.0 ± 0.2 | 64 ± 5 Shore D |
| 12 | 4.5 ± 0.5 | 1.1 ± 0.2 | 64 ± 5 Shore A |
| 13 | 5.0 ± 0.5 | 1.1 ± 0.2 | 64 ± 5 Shore A |
| 14 | 5.8 ± 0.5 | 1.1 ± 0.2 | 64 ± 5 Shore A |

Table II provides information for the inner shell layers of 14 example model orthotics. The inner shell layers of the example models have at least two different types of Shore hardness, e.g. the inner shell layer may have a Shore hardness of 95±5 Shore A. Alternatively, the inner shell layer may have a Shore hardness of 64±5 Shore D. All of the example inner shell layers are made from thermoplastic polyurethane. In some models, the inner shell has the same hardness as the corresponding outer shell layer, while in other models, the inner shell is harder or softer than the corresponding outer shell layer. The thickness of the example inner shell layers may vary from about 0.8 mm to about 1.4 mm. The weight of the inner shell layer 401 may be about 2.9 g to about 6.3 g.

Figure 8:
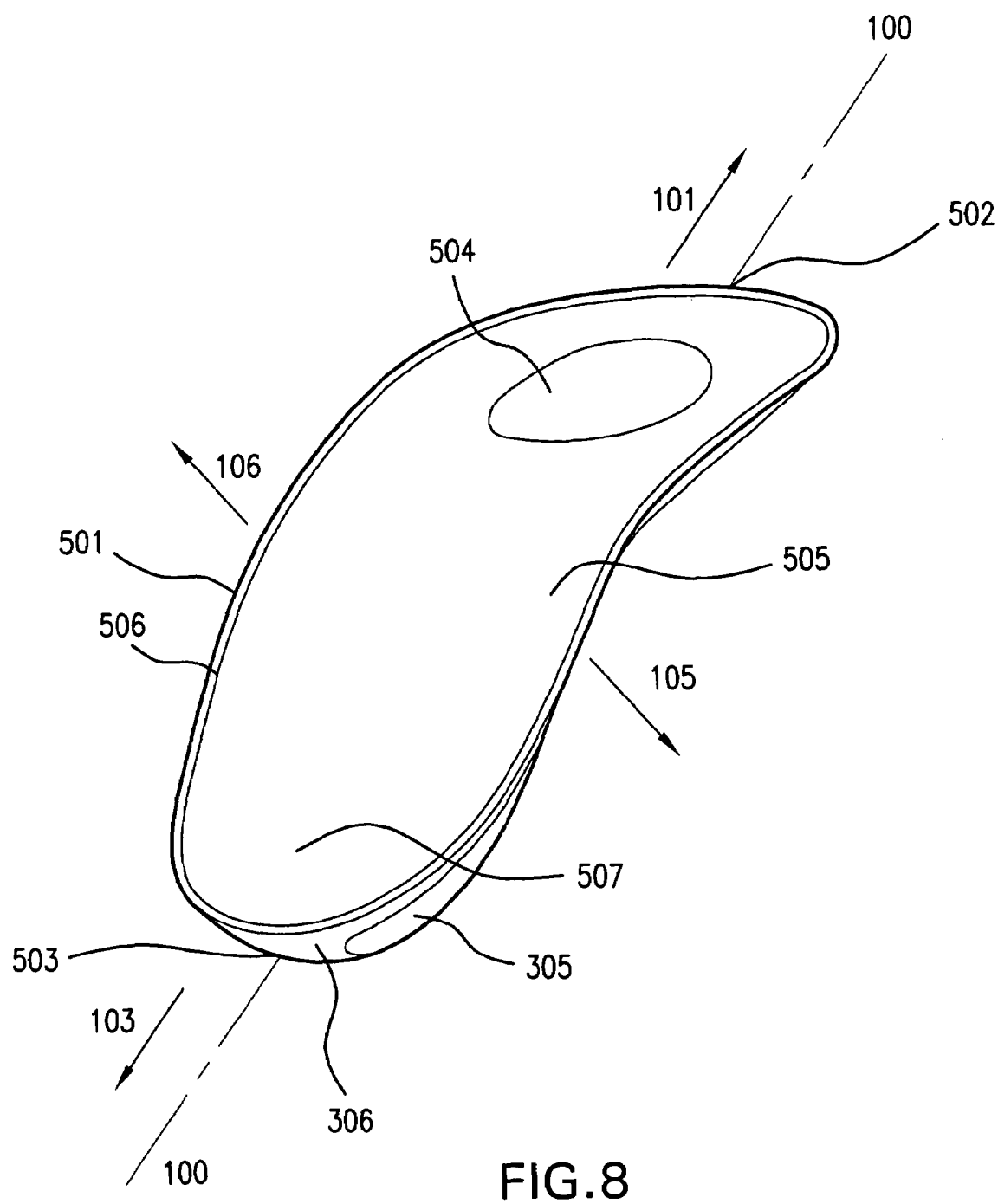
FIG. 8 depicts a top view of the example orthotic, according to the example embodiment of the present invention.

FIG. 8 depicts a top perspective view of the example orthotic, according to an example embodiment of the present invention. It will be appreciated that because this is a top perspective view, only the molded cushioning layer 501 and one of the projecting extensions 305 of the outer shell layer 301 at the heel region are visible. It will be appreciated that the molded cushioning layer 501 may provide support and comfort to the feet. The molded cushioning layer 501 may be constructed from a foamed material that is relatively resilient to stress and light in weight. The foamed material may be deformable when stressed, e.g., when the foot strikes during ambulation, and yet have sufficient memory to return to its original state. The molded cushioning layer 501 may also be constructed from thermoplastic olefin polymer, e.g., polyethylene, polypropylene, polyurethane, or elastomer. For example, a cast urethane foam which is a mixture of isocyanate, polyol, pigments, and stabilizer may be employed, e.g., SR-1088 A/B with a 1:3.6 mixing ratio, from the Praise Victor Industrial Co., Ltd. of Taichung Taiwan. The example foam may be chosen to have a minimum tear strength of approximately 10 lb/in. Other cushioning materials include graphite, closed-cell polyethylene foams, or opened-cell polyethylene foams. Other suitable examples of closed-cell polyethylene foams include Plastizote, Enduro™, Super-All-Step or Korex. The molded cushioning layer 501 of the example orthotic may be an integral piece molded from a single material or a multi-laminate constructed by using multiple layers of the same or different types of material. By integral, it is meant to imply that the molded cushioning layer of the example orthotic is molded as a single continuous unit with no divided parts.

Table III provides additional data for fourteen example models of the example orthotic. The example entries in Table III correspond to the same models that were described in Tables I & II. Exemplary lengths of the example orthotic measured along the centerline axis 100, may be about 160 mm to about 220 mm. (See, Table III, column 3). The heel thickness is measured at the center of the heel of the cushioning layer, approximately 38 mm from the back of the insole heel on the centerline. The insole length is measured along the centerline. The cushioning layer weight is the weight of the molded cushioning layer without the shells. The heel thickness may be about 5 mm to about 10 mm when measured at the at the center of the heel of the cushioning layer and may vary between 38-40 mm from the back of the orthotic of the centerline 100, depending on the particular model).

TABLE III

Specification of Example Orthotics Cushioning Layers

| Product Nos. | Heel Thickness (mm) | Insole Length (mm) | Cushioning Layer Weight (g) |
| --- | --- | --- | --- |
| 1 | 7.5 ± 1.0 | 172 ± 5.0 | 26.5 ± 3 |
| 2 | 8.0 ± 1.0 | 182 ± 5.0 | 30.5 ± 3 |
| 3 | 8.0 ± 1.0 | 194 ± 5.0 | 35.5 ± 3 |
| 4 | 7.5 ± 1.0 | 172 ± 5.0 | 26.5 ± 3 |
| 5 | 8.0 ± 1.0 | 182 ± 5.0 | 30.5 ± 3 |
| 6 | 8.0 ± 1.0 | 194 ± 5.0 | 35.5 ± 3 |
| 7 | 7.5 ± 1.0 | 172 ± 5.0 | 31.5 ± 3 |
| 8 | 8.0 ± 1.0 | 182 ± 5.0 | 37.5 ± 3 |
| 9 | 8.0 ± 1.0 | 194 ± 5.0 | 42.5 ± 3 |
| 10 | 8.4 ± 1.0 | 208 ± 5.0 | 47.5 ± 3 |
| 11 | 7.5 ± 1.0 | 172 ± 5.0 | 31.5 ± 3 |
| 12 | 8.0 ± 1.0 | 182 ± 5.0 | 37.5 ± 3 |
| 13 | 8.0 ± 1.0 | 194 ± 5.0 | 42.5 ± 3 |
| 14 | 8.4 ± 1.0 | 208 ± 5.0 | 47.5 ± 3 |

It will be appreciated that, as an alternative, the example orthotic may be configured to extend the entire length of the foot, from the forefoot region starting from the distal phalanges region to the hind foot region. Alternatively, the example orthotic may be configured from the middle, or proximal phalanges region to the distal part of the hind foot region, rather than completely under the user's heel.

The width of the example orthotic depicted in FIG. 8 is broadest at the distal end 502, and it gradually tapers towards the proximal end 503 to "cup" around the heel region of the user's foot. The depression around the heel region forms the heel cup 507. The heel cup 507 may provide support to the calcaneus bone region. The thickness of the cushioning layer 501 is thinnest at the distal end 502, and is about 0.5 mm to about 2 mm. The thickness of the cushioning layer 502 of the example orthotic gradually increases from the distal end 502 to the heel region at the proximal end 503, where it is at its thickest.

The cushioning layer 501 at the heel region extends downwards towards the bottom to form an integrally molded protruding heel piece 508. The protruding heel piece 508 may extend downwards into the receiving enclosure 302 of the outer shell layer 301. By integrally molded, it is understood that the protruding heel piece is formed as a single continuous extension from the molded cushioning layer 501. It will also be appreciated that the protruding heel piece 508 may alternatively be attached as a separate piece at the heel region, rather than being integrally formed as part of the cushioning layer. The heel piece 508 may be of any shape, e.g., it may be a round-, square-, oval-, or oblong-shaped piece. The heel piece 508 may also be U-shaped, C-shaped, or ¾-crescent-shaped piece with one end of the crescent slightly longer than the other to form a "spur" 307 at the lateral side. Both the heel piece 508 and the heel cup 507 may provide support for the entire calcaneus bone region. Alternatively, the heel piece 508 and the heel cup 507 may provide support to the central part of the calcaneus bone region.

FIG. 8 also shows that the molded cushioning layer 501 may be raised to form an upwardly convex protrusion 504 between the second and fourth metatarsal region at the distal end of the orthotic 502. The convex protrusion 504 may be configured to press against the soft tissues and muscles around the metatarsal region. The convex protrusion 504 may provide cushioning and support to the metatarsal region. The convex protrusion may also act to massage the soft tissue around the metatarsal region.

At the midfoot region of the example orthotic, the molded cushioning layer 501 may have an upturned medial flange 505. The medial flange 505 may wrap around the foot from the medial side towards the heel portion and the lateral side. The upturned medial flange 505 of the molded cushioning layer 501 is parallel to the upturned medial flange 309 of the outer shell layer 301. The upturned medial flange 505 of the molded cushioning layer 501 in combination with the upturned medial flange 309 of the outer shell layer 301 may provide support to the arch region. In addition, the upturned medial flanges of the cushioning 501 and outer shell 301 layers may prevent pronation of the foot.

The bottom surface of the molded cushioning layer 501 may be operably attached to the top surface of the outer shell layer 301, with or without an inner shell layer 401. The top surface of the molded cushioning layer 501 may be operably attached to the bottom surface of the covering layer 506. Approaches to operably attaching the bottom surface of the covering layer 506 to the top surface of the molded cushioning layer 501 include the use of a adhesive, heat, pressure, microwave, radiation, and others, with or without a thermoplastic polyurethane film.

The covering layer 506 has a top surface, and a bottom surface and extends the full length of the example orthotic. Alternatively, the covering layer 506 need not be present, or may cover only a portion of the orthotic. The covering layer 506 may be constructed from a fabric material, which may be stain-resistant, or abrasion resistant. The fabric material may be a natural fabric material or a synthetic fabric material. Further, the covering layer 506 may be a non-allergenic material, or a biocompatible material. For example, the covering layer 506 may be constructed from natural fabric, e.g., a cotton fabric, a wool fabric, a linen fabric, a hemp fabric, or a ramie fabric. The covering layer 506 may also be constructed from synthetic fabric, such as nylon, Dacron®, polyester, acetate, or felt material. In another example, the covering layer 506 may be a polyester knit fabric with a suede look.

Figure 9:
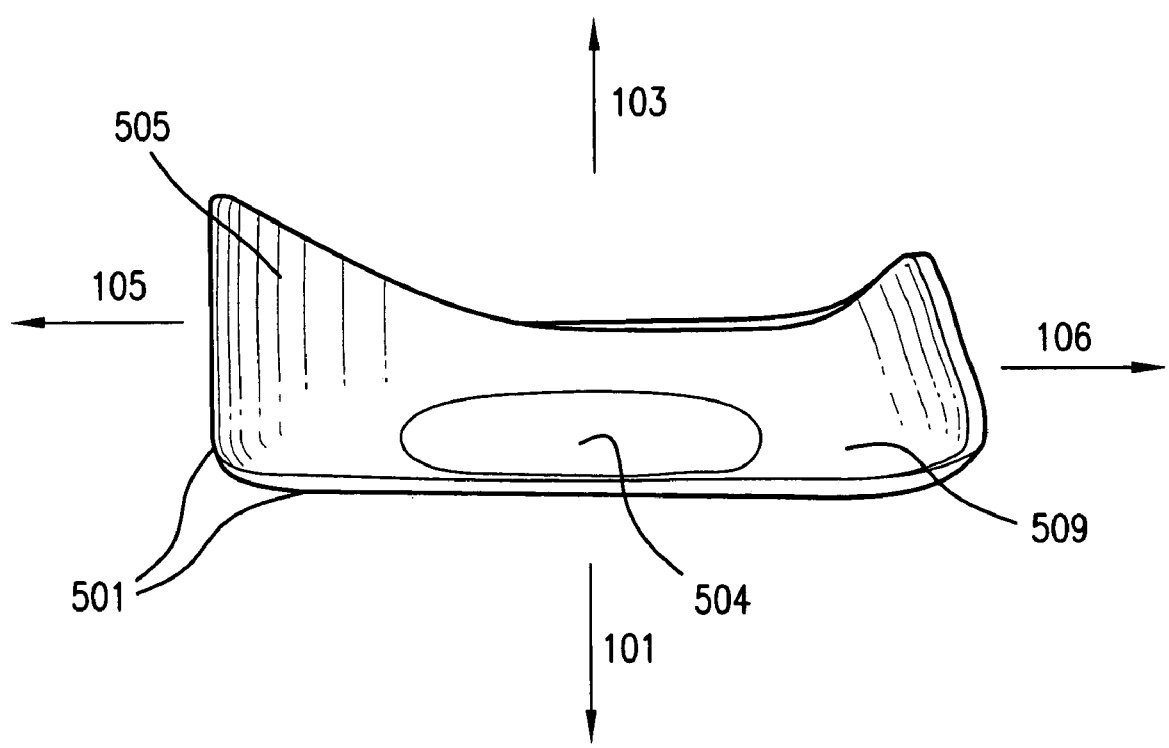
FIG. 9 depicts a distal top view of the example orthotic, according to the example embodiment of the present invention.

FIG. 9 depicts a distal top view of the example orthotic, according to an example embodiment of the present invention. As shown, it will be appreciated that the medial region where it turns outwards and upwards to form the upturned medial flange 505 of the cushioning layer 501 is substantially wider than at the lateral side 509. The raised convex protrusion 504 is shown relative to the direction of the example orthotic.

Figure 10:
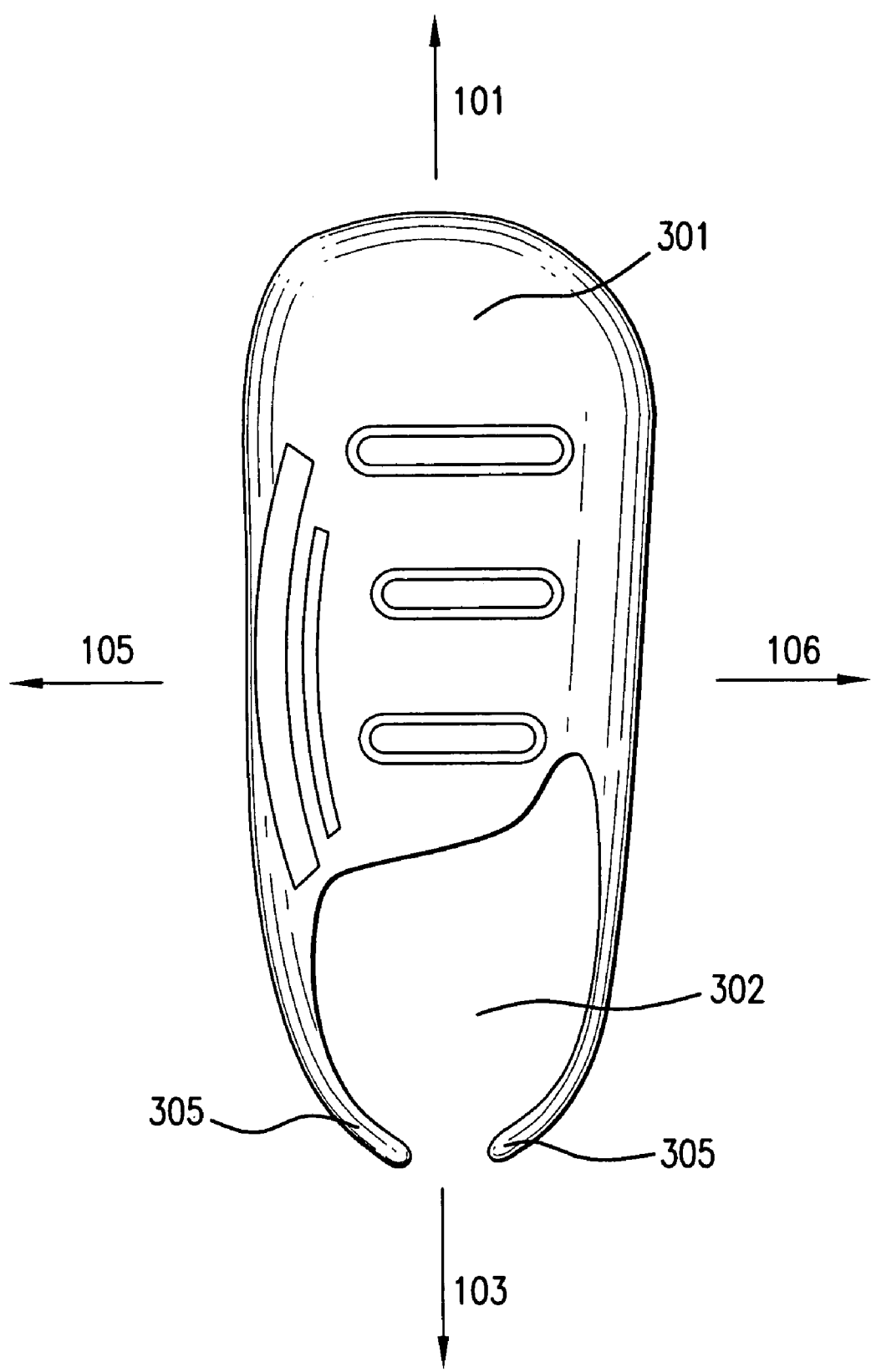
FIG. 10 depicts an outer shell layer of a second example orthotic, according to an alternative example embodiment of the present invention.

FIG. 10 depicts a second example orthotic, according to a first alternative example embodiment of the present invention. In the second example orthotic, the outer shell layer 301 is essentially similar in the first example orthotic described in FIG. 6. However, in the second example orthotic, the pair of projecting extensions 305 of the outer shell layer 301 may be joined at their ends to form a continuous piece around the back. (Compare FIG. 10 with that of FIG. 6). Thus, in the example orthotic of the second embodiment, the outer shell layer 301 is constructed with a cut-out receiving enclosure 302 defining an aperture through the outer shell layer 301 at the heel region.

Figure 11:
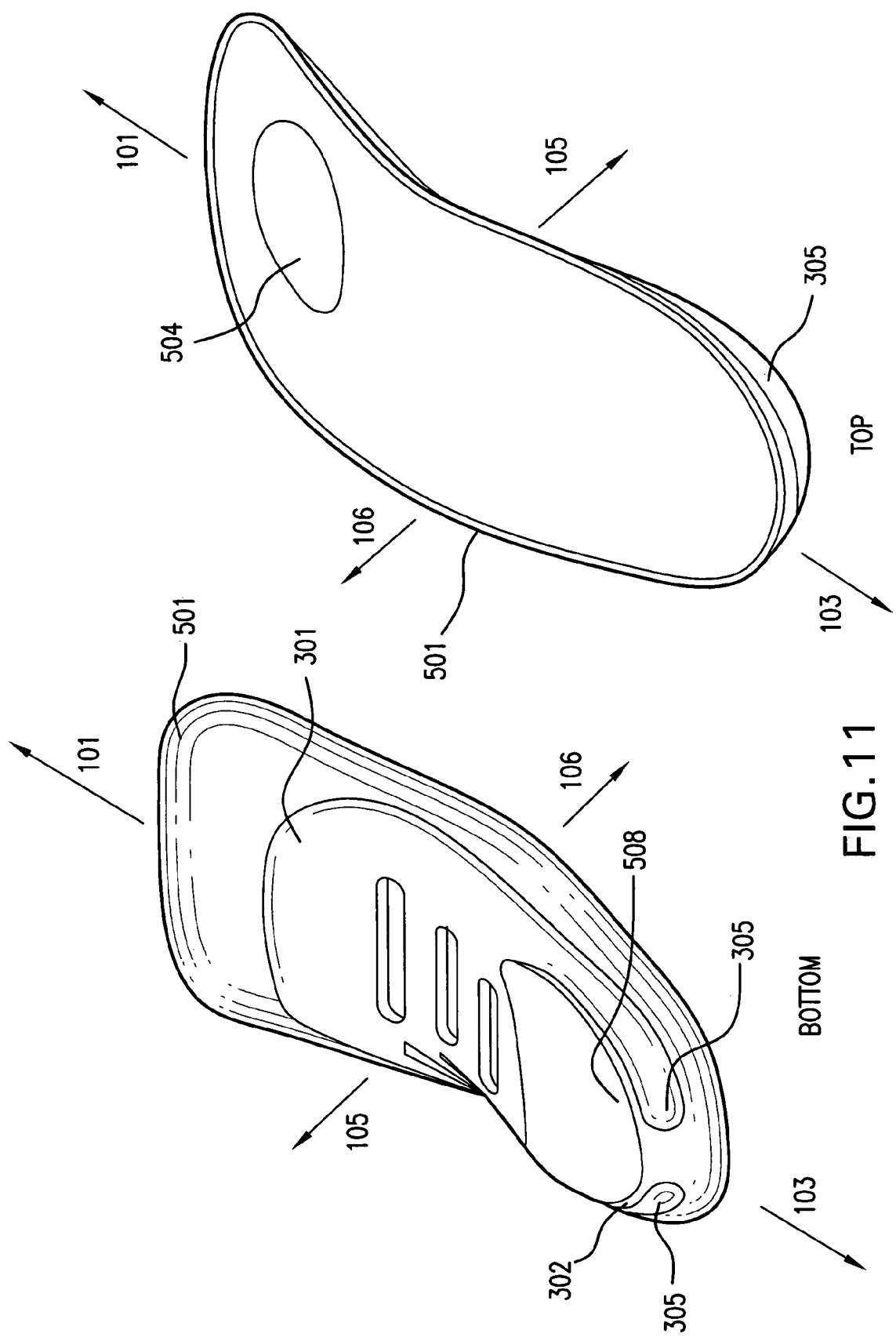
FIG. 11 depicts a bottom and a top perspective of the second example orthotic, according to the alternative example embodiment of the present invention.

FIG. 11 depicts a bottom and a top perspective of the second example orthotic, according to the first alternative example embodiment of the present invention. The outer shell layer 301 of the second example orthotic may be a single continuous piece, where the ends of the projecting extensions are joined. The outer shell layer 301 in the second example orthotic may extend from at least the metatarsal of the user's foot to the heel region. The outer shell layer 301 may have a receiving enclosure 302 defining an aperture through the outer shell layer 301. The receiving enclosure 302 is the region of the outer shell layer for receiving the protruding heel piece 508 of the cushioning layer 501. The projecting extensions 305 of the outer shell layer 301 may be molded to form a joined continuous piece, embracing the back of the heel piece 508. (See, FIG. 11, Bottom). The outer shell layer 301 of the second example orthotic, according to the second alternative example embodiment, is operably attached to the molded cushioning layer 501 having an upwardly raised convex protrusion 504 between the second and fourth metatarsal region. A partial view of the projecting extension 305 of the outer shell layer 301 embracing the heel region of the cushioning layer 501 is shown in FIG. 11, Top.

Figure 12:
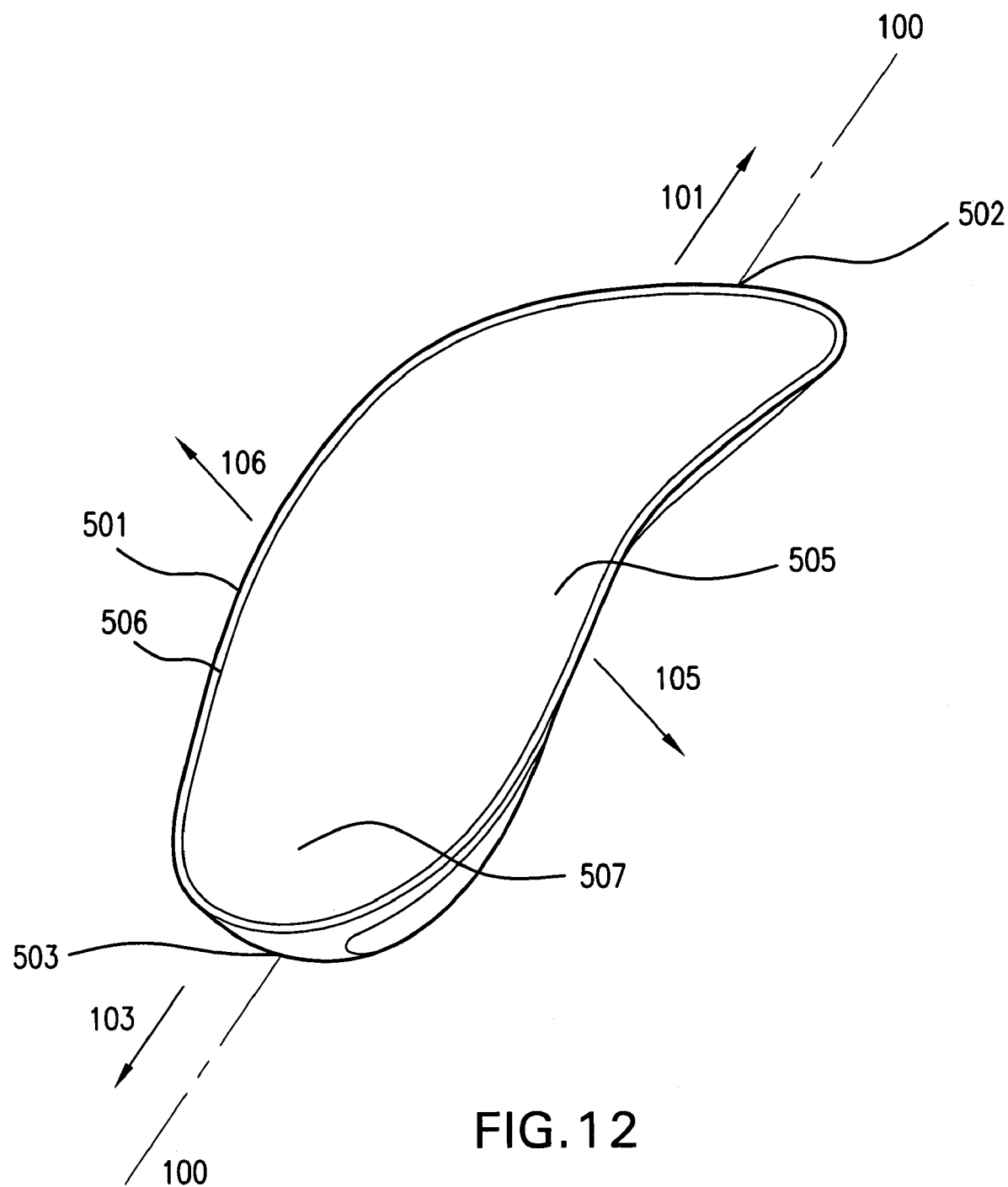
FIG. 12 depicts a third example orthotic, according to a second alternative example embodiment of the present invention.

FIG. 12 depicts a top perspective view of a third example orthotic, according to a second alternative example embodiment of the present invention. The third example orthotic need not have an upwardly raised convex protrusion between the second and fourth metatarsal region at the distal end 502 of the orthotic. Instead, the molded cushioning layer 501 at the distal end 502 is a continuous flat piece. The molded cushioning layer 501 of the third example orthotic may also include a heel cup 507 at the proximal end 503 of the orthotic. It will be appreciated that, although the third example orthotic is illustrated as having an upturned medial flange 505 and a covering layer 506, alternative versions may be provided without these features.

Figure 13:
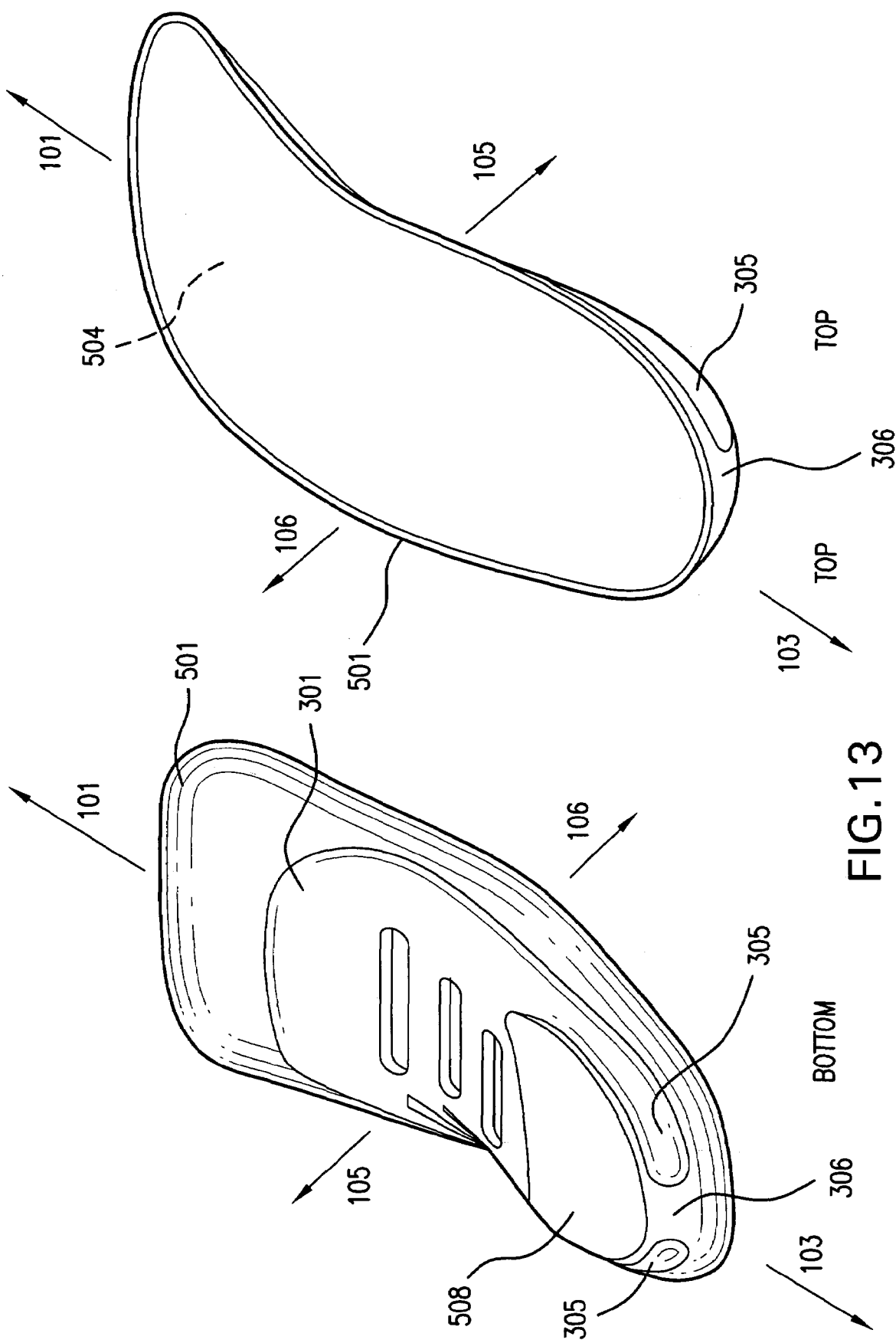
FIG. 13 depicts a bottom and a top perspective of the third example orthotic, according to the second alternative example embodiment of the present invention.

FIG. 13 depicts a bottom and a top perspective of the third example orthotic, according to the second alternative example embodiment of the present invention. As depicted in FIG. 13, the molded cushioning layer 501 need not have an upwardly raised convex protrusion 504 between the second and fourth metatarsal region (See, FIG. 13 Top). The molded cushioning layer 501 as shown in FIG. 13 may be fixedly attached to an outer shell layer 301 having a pair of projecting extensions 305 that need not be joined at their ends, thus exposing a "gap" 306 of the molded cushioning layer 501 at the back of the heel region. (See, FIG. 13 Bottom)

Figure 14:
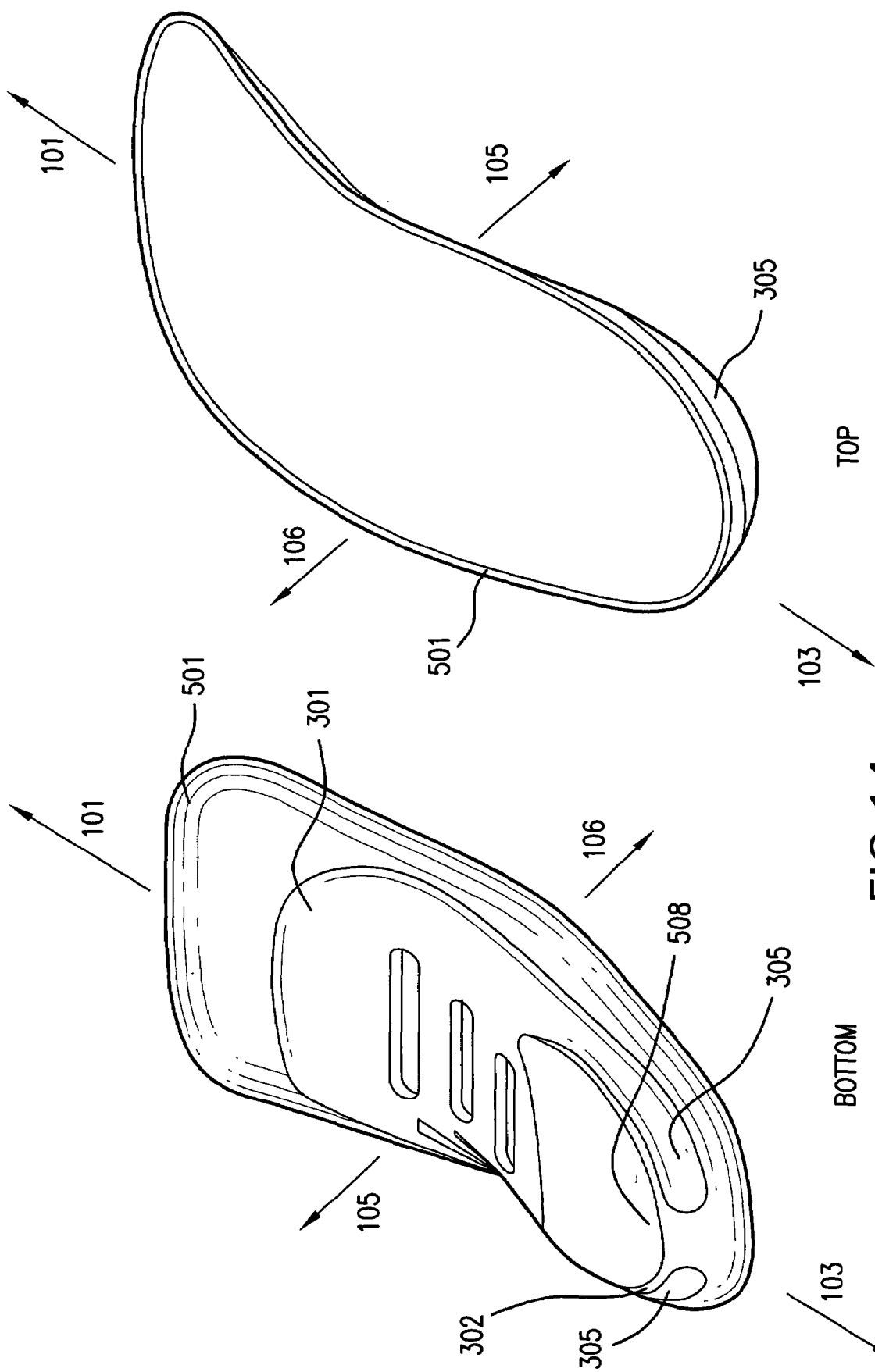
FIG. 14 depicts a bottom and a top perspective of a fourth example orthotic, according to a third alternative example embodiment of the present invention.

FIG. 14 depicts a bottom and a top perspective of the fourth example orthotic, according to the third alternative example embodiment of the present invention. The fourth example orthotic may have a molded cushioning layer 501 that lacks the upwardly raised convex protrusion 504 between the second and fourth metatarsal region (See, FIG. 14 Top). The cushioning layer 501 may be combined with the outer shell layer 301 that have a pair of projecting extensions 305 joined at their ends at the back of the heel region. (See, FIG. 14 Bottom). The outer shell layer 301 may be configured as a continuous outer shell layer 301 with a cut-out receiving enclosure 302 defining an aperture through the outer shell layer 301. The protruding heel piece 508 extends through the receiving enclosure 302 of the outer shell layer 301.

FIG. 15 depicts a bottom perspective of the heel piece of the fifth and sixth example orthotics according to the fourth alternative example embodiment of the present invention. The fifth example orthotic may have a molded cushioning layer 501 that have a protruding heel piece 508 which supports the entire calcaneus bone region (FIG. 15A). Alternatively, the molded cushioning layer 513 may have a protruding heel piece 514 that supports only the central portion of the calcaneus bone region (FIG. 15B). Both example orthotics having either a protruding heel piece 508 or 514 may have projecting extensions 305A or 305B of the outer shell layer joined at the ends. Alternatively, the projecting extensions 305A or 305B may be unjoined at the ends. As depicted in FIG. 15A, the heel region 508 is larger in area than the heel region 514 of FIG. 15B.

Figure 16A:
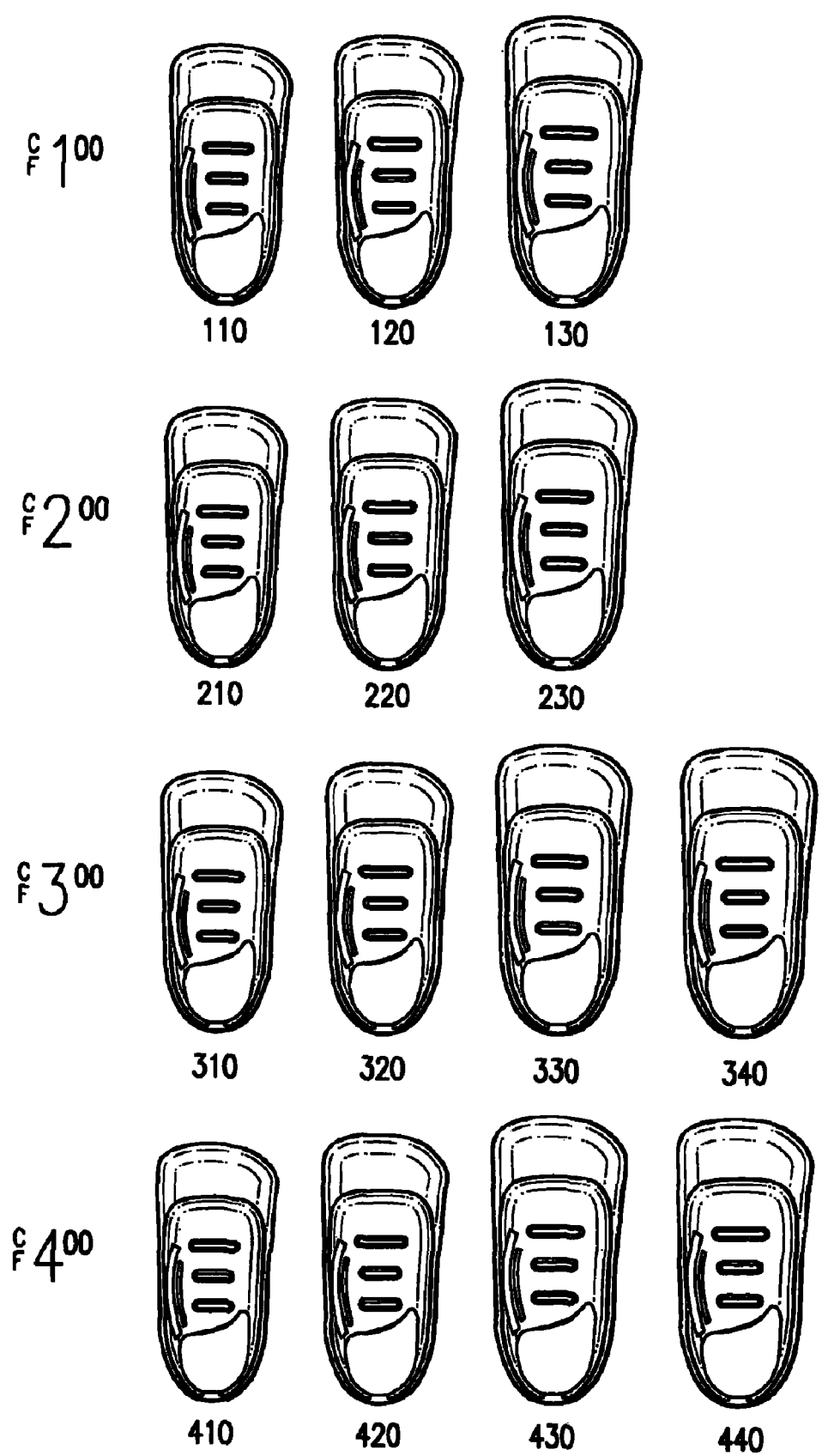
FIG. 16A illustrates an example display set of orthotics of the pre-manufactured model orthotics, according to an example embodiment of the present invention.

FIG. 16 illustrates an example display set of pre-manufactured orthotics, according to an example embodiment of the present invention. The display set is depicted in an unpackaged form in FIG. 16A. It will be appreciated that the different models in the example display set may also be provided packaged in pairs of matching left and right orthotics of the same model (See, FIG. 16B). The example display set may include a plurality of different orthotics, e.g., the 14 different example model orthotics, with characteristics described previously in Tables I-III Each orthotic in the example display set may, but need not, have a substantially similar design, although the exact dimensions and material properties of the different models of orthotic in the display set may vary. For example, each orthotic in the display set may include a molded cushioning layer 501 and a supporting outer shell layer 301, as illustrated above in FIGS. 1-8, or one of the alternative example embodiments. All of the models in the set may be similar to the embodiments in FIGS. 1-8, or other embodiments that may be used alone or in combination.

The set of pre-manufactured cushioned orthotics may be a "¾ length" orthotic. The set of pre-manufactured orthotics may be a plurality of orthotics or display set of orthotics which may vary in length, width, cushioning and in the amount of arch support provided. (See, FIG. 16A). The display set of orthotics may include orthotic models having different respective lengths depending on the length of the user's foot. For example the display set of orthotics may have at least four different lengths: a first length that may be the shortest length, a second length which may be longer than the shortest length, a third length, which may be longer relative to the second length and a fourth length which may be the longest length.

The example display set of orthotics having different lengths may be manufactured having different arch heights with varying hardness, stiffness, or dimensions. For example, users without a defined arch or with a low arch may need more support and may prefer greater hardness. On the other hand, users with a high arch or an arch that is more defined may prefer more cushioning than hardness. A greater degree of support due to a harder or stiffer outer and inner shell layers may even be uncomfortable to a user with a high arch because, as their arch is defined, the harder shell layers may stick into the arch which may become sensitive to the hard feeling underneath the foot. In some example embodiment, the arch support may have at least two different levels of arch support having different hardness.

The example display set of orthotics having different lengths may be composed of a cushioning layer and an arch support with different arch heights. The cushioning layer may be manufactured from foam of at least two different firmness, a soft cushion layer and a firmer cushion layer. The orthotic models of all different lengths in the example orthotic display set may be manufactured from a firmer foam, except for the orthotic model having the longest length, which may not be manufactured from the softest foam.

The example display set of orthotics having the same lengths may have at least two orthotic models with different size arch supports and/or material. In another example embodiment, the arch supports of different materials for the orthotic models of a particular length of the example display set of orthotics may be substantially dimensionally identical.

Some example set of pre-manufactured orthotics, according to some example embodiments of the present invention, there may be different models having different lengths combined with different firmness of the cushioning layer and levels of arch support. For example, at least one of the orthotic models may be composed of fourteen different models with at least four different lengths. There may be a first model series with the softest cushioning layer and the lowest level of arch support (See, FIG. 16A, "The 100 series"), a second model series with the softest cushioning layer and a higher level of arch support ("The 200 series), a third model series with a firmer cushioning layer and the lowest level of arch support ("The 300 series"), and a fourth model with a firmer cushioning layer and a higher level of arch support ("The 400 series").

In another embodiment of the example set of pre-manufactured cushioned orthotics in the example display set of orthotics, the first model may have a shortest length with the softest cushioning layer, and the lowest level of arch support. In a second model, the orthotic with the shortest length and the softest cushioning layer may have a higher level of arch support. Alternatively, a third model orthotic with the shortest length may have a firmer cushioning layer, combined with the lowest level of arch support and a fourth model orthotic with the shortest length may have a firmer cushioning layer, and a higher level of arch support.

Another embodiment of the example set of pre-manufactured cushioned orthotics in the example display set of orthotics may have a second length longer than the shortest length. For example, the fifth model may have a second length that is longer than the shortest length combined with the softest cushioning and the lowest level of arch support. A sixth model with the second length and the softest cushioning layer may have the higher level of arch support. Alternatively, a seventh model with the second length may have a firmer cushioning layer and the lowest level of arch support, while an eighth model with the second length may have a firmer cushioning layer, and a higher level of arch support;

The example set of pre-manufactured cushioned orthotics in the example display set of orthotics may also have a third length that is longer relative to the second length. The example cushioned orthotic sets may be manufactured with the softest or a firmer foam in combination with either a lower or higher arch support. For an example, a ninth model with a third length that is longer than the second length orthotics may have the softest cushioning layer with the lowest level of arch support. A tenth model with the third length may have the softest cushioning layer and a higher level of arch support while an eleventh model may have a firmer cushioning layer with the lowest level of arch support, and a twelfth model may have the firmer cushioning layer and the higher level of arch support;

The example set of pre-manufactured cushioned orthotics in the example display set of orthotics may also have a fourth length which may be the longest length in the set. For example, a thirteenth model with the longest length may be manufactured with the firmer cushioning layer and the lowest level of arch support. In addition, a fourteenth model having the longest length may be combined with the firmer cushioning layer, and the higher level of arch support.

Although the combined total of 14 example models in the example display set of orthotics have been found to provide an acceptable fit for the vast range of potential users, it will be appreciated that additional or fewer models may be included. For example, each of the 14 example models in the example display set of orthotics may have different combinations of outer shell layer 301 and inner shell layer 401 hardness, and/or different thickness and size at the heel piece 508 or 513. The 14 example models in the example display set of orthotics may also have an upwardly raised convex protrusion 504 between the second and fourth metatarsal region and may be of different heights.

Figure 17:
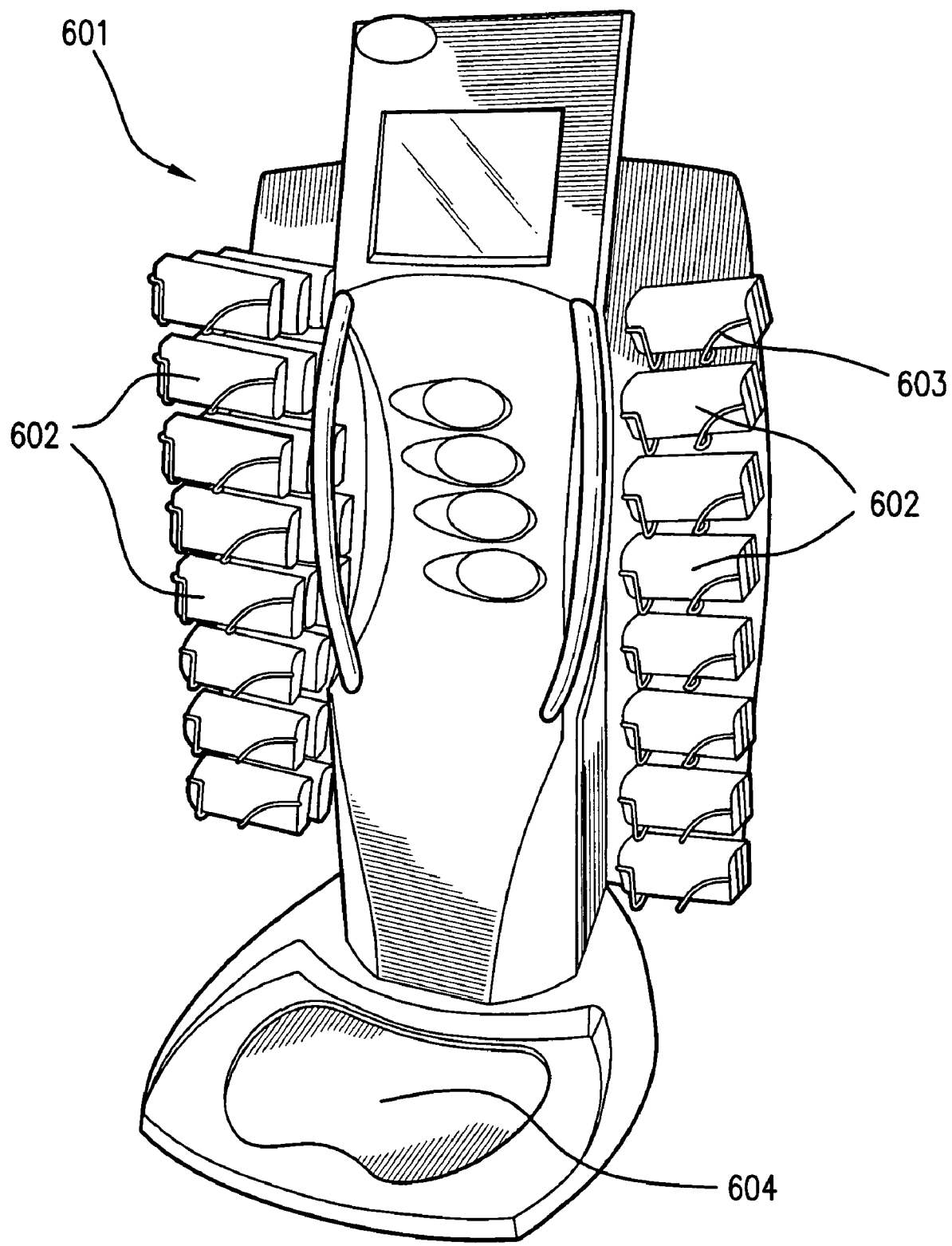
FIG. 17 illustrates an example display including the example display set of pre-manufactured orthotics, according to an example embodiment of the present invention.

FIG. 17 illustrates an example display 601 including the example display set of pre-manufactured orthotics 602. The display includes packaged pairs of different model orthotics 602 of the example display set of orthotics described above that are removably attached to the display. The packaging and/or the display may prominently indicate the attributes of each particular model in the display set. The display sets of pre-manufactured orthotics are "removably disposed" in a manner that is visible and easily accessible to potential customers.

For example, in one embodiment of the example display, the set of pre-manufactured orthotic removably disposed on the display may include a plurality of different orthotic models, such as the 14 different models described above. The set of pre-manufactured orthotics may be "¾ lengths" orthotics with different respective lengths depending on the length of the user's foot and different respective levels of arch support. For example, different orthotic models having the same length may have different arch support manufactured from different arch support material and substantially the same arch support dimension. The different orthotic models of the same length may also have substantially similar external designs and color pattern. Alternatively, orthotics of the same support type but of different sizes may have the same color pattern.

Although the removably disposed orthotics are held in place by wired racks 603 as illustrated in FIG. 17, it will be appreciated that other approaches to removable attachments may be employed, e.g., see-through drawers or cases, a windowed vending or dispensing machine, etc. The display sets may also be "shelved" by hooks, rods, etc. The example display of FIG. 17 may be provided as part of an electronic kiosk which performs procedures for measuring a user and recommending particular particular orthotics to the user. The example kiosk includes a measurement device 604 on which a user stands to have their foot measured. This electronic kiosk and example procedures are described in a concurrently filed application Footcare Product Dispensing Kiosk, filed U.S. application Ser. No. 11/524,745, filed Sep. 21, 2006, assigned to Schering-Plough Healthcare Products, Inc. the assignee of the present application, the entire contents of which are hereby incorporated by reference thereto.

Several embodiments of the present invention are specifically illustrated and described herein. However, it will be appreciated that modifications and variations of the present invention are covered by the above teachings and within the purview of the appended claims without departing from the spirit and intended scope of the invention.

We claim:

1. An orthotic, comprising:
   a covering layer on the top surface;
   a foam cushioning layer fixedly coupled to the covering layer, the foam cushioning layer configured to extend from at least the proximal metatarsal region to the proximal heel region, the cushioning layer being at its thinnest towards the proximal metatarsal region and thickest at the proximal heel region, the cushioning layer having a protruding heel piece integrally molded as part of the cushioning layer at the proximal heel region, and an upturned medial flange extending towards the proximal heel portion, wrapping around to the opposite lateral side, and tapering towards the distal forefoot portion;

an outer shell layer fixedly coupled to the cushioning layer, the outer shell layer configured to extend longitudinally from at least the medial cuneiform-first metatarsal joint region to the calcaneus bone region of the user, the outer shell layer further having an upturned flange on the medial side, parallel to the upturned medial flange of the cushioning layer, an enclosure defining a aperture therethrough at the heel region, the enclosure configured to receive the integral protruding heel piece of the cushioning layer, and an inner shell insert layer operably attached between the cushioning layer and the outer shell layer, the inner shell insert layer extending from at least the medial cuneiform-first metatarsal joint region to the talus-navicular joint region and not extending to the proximal heel region of the user.

2. The orthotic of claim 1, wherein the inner shell insert layer comprises a thermoplastic material.

3. The orthotic of claim 2, wherein the thermoplastic material is thermoplastic urethane.

4. The orthotic of claim 1, wherein the cushioning layer comprises a foamed material.

5. The orthotic of claim 4, wherein the foamed material is thermoset polyurethane foam.

6. The orthotic of claim 1, wherein the cushioning layer forms a heel cup at the proximal end.

7. The orthotic of claim 1, the outer shell layer further comprising a plurality of perforations in the mid portion of the outer shell layer.

8. The orthotic of claim 7, wherein the perforations in the mid portion of the outer shell layer comprises a plurality of parallel slots extending from the medial side to the lateral side.

9. The orthotic of claim 1, the foam cushioning layer further comprising a raised convex protrusion at the distal forefoot region between the second to fourth metatarsal.

10. An orthotic, comprising:

a covering layer on a top surface;

a foam cushioning layer fixedly coupled to the covering layer, the foam cushioning layer is configured to extend from at least the proximal metatarsal region to the proximal heel region, the cushioning layer being thinnest at the distal forefoot region and thickest at the heel region, the cushioning layer having an upwardly raised convex protrusion between the second and fourth metatarsal, the cushioning layer further having a heel region with a protruding heel piece integrally formed as part of the foam cushioning layer, the protruding heel piece supporting the entire heel region and an upturned medial flange extending towards the proximal heel portion, wrapping around to the opposite lateral side, and tapering towards the distal forefoot portion;

an outer shell layer fixedly coupled to the foam cushioning layer, the outer shell layer is configured to extend longitudinally from at least the medial cuneiform-first metatarsal joint region to the talus-navicular bone region, extending on either side around the calcaneus bone portion, the outer shell layer at the calcaneuous bone region cut out to form an enclosure defining a aperture therethrough for receiving the protruding heel piece, the outer shell layer extending on either side of the calcaneous region a pair of projecting extensions having a first end and a second end, the projecting extensions embracing the heel piece on either side with the first end and the second end terminating just behind the heel region, the outer shell layer further having an upturned medial flange, parallel to the upturned flange of the cushioning layer; and an inner shell insert layer operably attached between the cushioning layer and the outer shell layer, the inner shell insert layer extending from at least the medial cuneiform-first metatarsal joint region to the talus-navicular joint region and not extending to the proximal heel region of the user.

11. An orthotic, comprising:

a covering layer on a top surface;

a foam cushioning layer fixedly coupled to the covering layer, the foam cushioning layer is configured to extend from at least the proximal metatarsal region to the proximal heel region, the cushioning layer is thinnest at the distal forefoot region and thickest at the heel region, the cushioning layer having an upwardly raised convex protrusion between the second and fourth metatarsal, the cushioning layer further having a heel region with a protruding heel piece integrally formed as part of the foam cushioning layer, the protruding heel piece supporting the entire heel region and an upturned medial flange extending towards the proximal heel portion, wrapping around to the opposite lateral side, and tapering towards the distal forefoot portion;

an outer shell layer fixedly coupled to the foam cushioning layer, the outer shell layer is configured to extend longitudinally from at least the medial cuneiform-first metatarsal joint region to the talus-navicular bone region, extending on either side around the calcaneus bone portion, the outer shell layer at the calcaneuous bone region cut out to form an enclosure defining a aperture therethrough for receiving the protruding heel piece, the outer shell layer extending on either side of the calcaneuos region a pair of projecting extensions having a first end and a second end, the projecting extensions embracing the heel piece on either side with the first end and the second end joined at the heel region, the outer shell layer further having an upturned medial flange, parallel to the upturned flange of the cushioning layer; and an inner shell insert layer operably attached between the cushioning layer and the outer shell layer, the inner shell insert layer extending from at least the medial cuneiform-first metatarsal joint region to the talus-navicular joint region and not extending to the proximal heel region of the user.

* * * * *